US011365392B2

(12) United States Patent
Zagury et al.

(10) Patent No.: US 11,365,392 B2
(45) Date of Patent: Jun. 21, 2022

(54) EX VIVO GENERATION OF MHCII RESTRICTED CD4+ FOXP3+ REGULATORY T CELLS AND THERAPEUTIC USES THEREOF

(71) Applicants: INSERM (Institut National de la Sante et de la Recherche Medicale), Paris (FR); Medecine et Innovation, Paris (FR); Universite Paris Diderot—Paris 7, Paris (FR); Centre National de la Recherche Scientifique (CNRS), Paris (FR)

(72) Inventors: Daniel Zagury, Paris (FR); Helene Le Buanec, Paris (FR); Sophie Duchez, Paris (FR); Valerie Schiavon, Paris (FR); Armand Bensussan, Paris (FR)

(73) Assignees: INSERM (INSTITUT NATIONAL DE LA SANTÉ ET DE LA RECHERCHE MÉDICALE), Paris (FR); MEDECINE ET INNOVATION, Paris (FR); UNIVERSITÉ PARIS DIDEROT—PARIS 7, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 111 days.

(21) Appl. No.: 16/320,745

(22) PCT Filed: Aug. 4, 2017

(86) PCT No.: PCT/EP2017/069823
§ 371 (c)(1),
(2) Date: Jan. 25, 2019

(87) PCT Pub. No.: WO2018/024894
PCT Pub. Date: Feb. 8, 2018

(65) Prior Publication Data
US 2019/0161728 A1    May 30, 2019

Related U.S. Application Data

(60) Provisional application No. 62/371,329, filed on Aug. 5, 2016.

(30) Foreign Application Priority Data

Oct. 28, 2016   (EP) ..................................... 16196425

(51) Int. Cl.
C12N 5/0783    (2010.01)
A61K 35/17     (2015.01)

(52) U.S. Cl.
CPC ............ *C12N 5/0637* (2013.01); *A61K 35/17* (2013.01); *C12N 5/0646* (2013.01); C12N 2501/01 (2013.01); C12N 2501/065 (2013.01); C12N 2501/15 (2013.01); C12N 2501/22 (2013.01); *C12N 2501/2302* (2013.01); *C12N 2501/2304* (2013.01); *C12N 2501/2307* (2013.01); *C12N 2501/2315* (2013.01); *C12N 2501/515* (2013.01); *C12N 2501/72* (2013.01); *C12N 2501/727* (2013.01); *C12N 2501/999* (2013.01); *C12N 2502/1121* (2013.01)

(58) Field of Classification Search
None
See application file for complete search history.

(56) References Cited

U.S. PATENT DOCUMENTS

2003/0157057 A1* 8/2003 Horwitz ................. A61K 35/17
                                                       424/85.1
2006/0115899 A1* 6/2006 Buckner ............. A61K 39/0008
                                                        435/372

(Continued)

FOREIGN PATENT DOCUMENTS

EP        2 408 934 B1    11/2014
WO    2010/022341 A1     2/2010
(Continued)

OTHER PUBLICATIONS

Sassone-Corsi, 2012, Cold Spring Harb Perspect Biol, pp. 1-3 Schmidt et al., Feb. 2016, pp. 1-31.*
Chaudhury et al., 2009, IUBMB Life vol. 61: 929-939 Lu et al., 2014, J. Immunol. Res. pp. 1-8.*
Delgoffe et al., 2009, Immunology, vol. 127: 459-465 Zhao et al., 2004, Leukemia, vol. 18: 285-292.*
Mahic et al., 2006, J. Immunol. vol. 177: 246-254 Baratelli et al., 2010, Am. J. Trans. Res. vol. 2: 356-367.*
Schenk et al., 2014, British. J. Canc. vol. 111: 2039-2045 El-Mowafy et al., 2003, Carcinogenesis, vol. 24: 869-873.*
Ballou et al., 2008, J. Chem. Biol. vol. 1: 27-36 Lu et al., 2014, PNAS, vol.*
Schmitt et al., 2013, Front. Immunol. vol. 4: 1-13 Scotta et al., 2013, Cell Ther. Immunother. vol. 98: 1291-1299.*

(Continued)

*Primary Examiner* — Amy E Juedes
(74) *Attorney, Agent, or Firm* — WCF IP

(57) ABSTRACT

The present invention relates to a method for ex vivo generating and expanding MHCII restricted CD4+ Foxp3+ regulatory T cells, and therapeutic uses thereof. The inventors here demonstrated the optimal conditions for inducing Foxp3 expression in naive CD3+ CD4+ TCRαβ+ MHCII restricted T following polyclonal or following antigen-specific activation. They also developed an experimental procedure to generate autologous CD8+ T cell lines functionally committed to lyse tumor-antigen specific FOXP3 expressing TCRαβ+ MHCII restricted T cells, pathogenic CD4+ T cells that favour tumor cell immune evasion. In particular, the present invention relates to a method for generating ex vivo MHCII restricted CD4+ Foxp3+ regulatory T cells having the following phenotype: CD3+ CD4+ Foxp3+.

3 Claims, 14 Drawing Sheets
Specification includes a Sequence Listing.

(56) References Cited

U.S. PATENT DOCUMENTS

| | | | |
|---|---|---|---|
| 2012/0009208 A1 | 1/2012 | Chauhan | |
| 2013/0142830 A1* | 6/2013 | Akbari | C12N 5/0637 424/275.1 |
| 2013/0195919 A1* | 8/2013 | Von Andrian | A61P 35/00 424/278.1 |
| 2019/0032014 A1* | 1/2019 | Alaniz | A61P 37/06 |

FOREIGN PATENT DOCUMENTS

| | | |
|---|---|---|
| WO | 2012/012737 A2 | 1/2012 |
| WO | 2013/050596 A1 | 4/2013 |

OTHER PUBLICATIONS

Dituri et al., 2019, Cell. vol. 8: E3432-E3440.*

Tran et al.; "Selective expression of latency-associated peptide (LAP) and IL-1 receptor type I/II (CD121a/CE121b) on activated human FOXP3+ regulatory T cells allows for their purification from expansion cultures"; Blood, vol. 113, No. 2, May 21, 2009, pp. 5125-5133.

Ohkura et al.; "FOXP3+ regulatory T cells: control of FOXP3 expression by pharmacological agents"; Trends in Pharmacological Sciences, vol. 32, No. 3, Mar. 1, 2011, pp. 158-166.

Chen et al.; "Conversion of Peripheral CD4+CD25− Naive T Cells to CD4+CD25+ Regulatory T Cells by TGF-beta Induction of Transcription Factor Foxp3"; The Journal of Experimental Medicine, vol. 198, No. 12, Dec. 15, 2003, pp. 1875-1886.

Baratelli et al.; "Prostaglandin E2 Induces FOXP3 Gene Expression and T Regulatory Cell Function in Human CD4+ T Cells"; The Journal of Immunology, vol. 175, No. 3, Jul. 20, 2005, pp. 1483-1490.

Scott et al.; "Patterns of membrane TcR$\alpha\beta$ and TcR$\gamma\delta$ chain expression by normal blood CD4+CD8−, CD4−CD8dim+ and CD4−CD8− lymphocytes"; Immunology, vol. 70, Jan. 1, 1990, pp. 351-356.

* cited by examiner

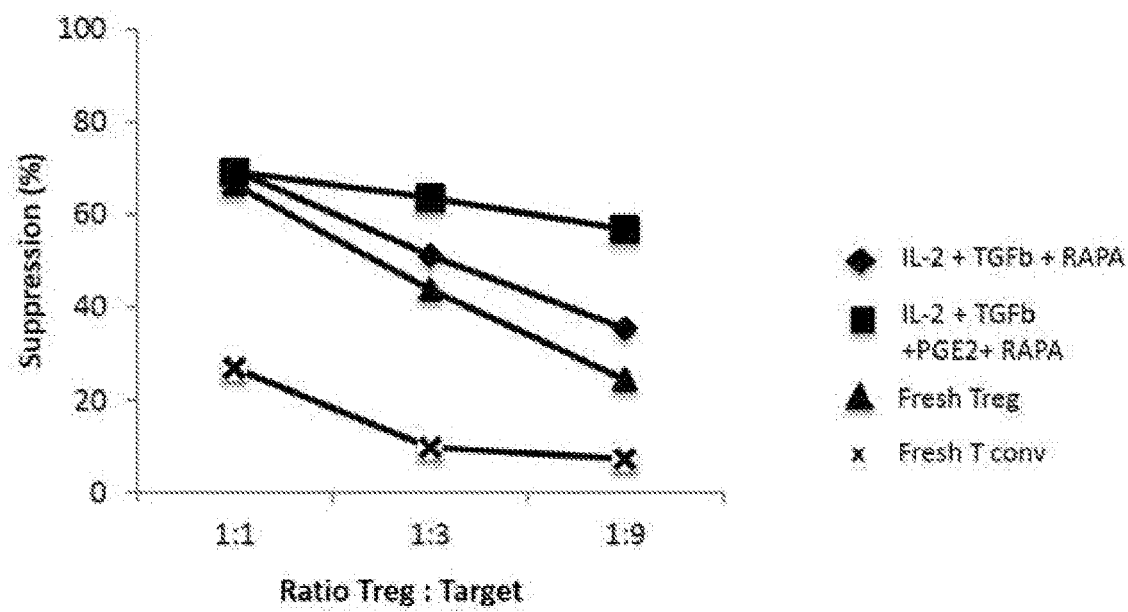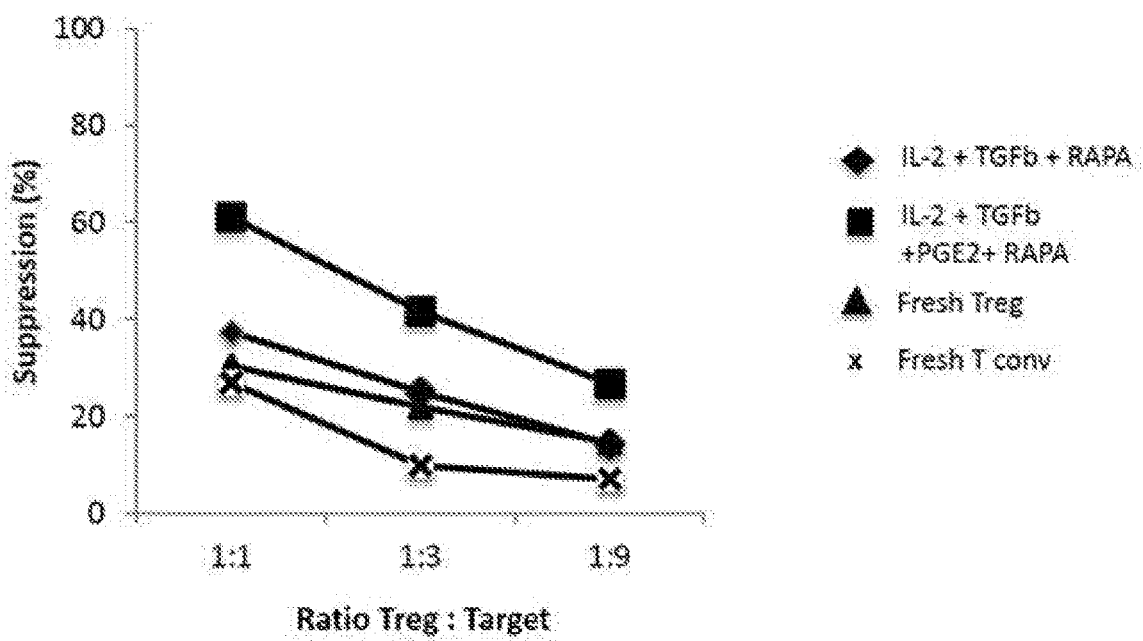
FIG. 3

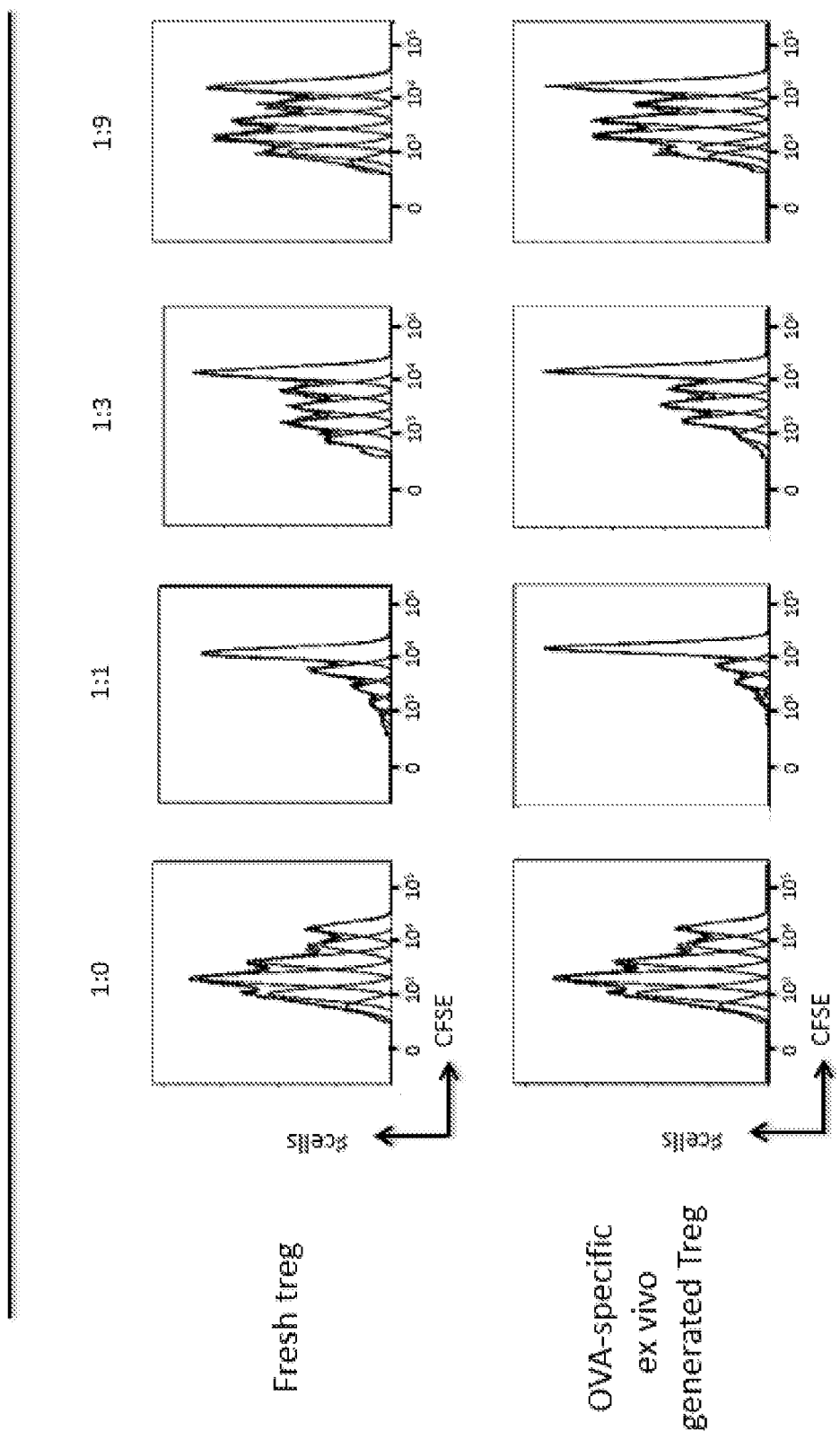
FIG. 7 (1/2)

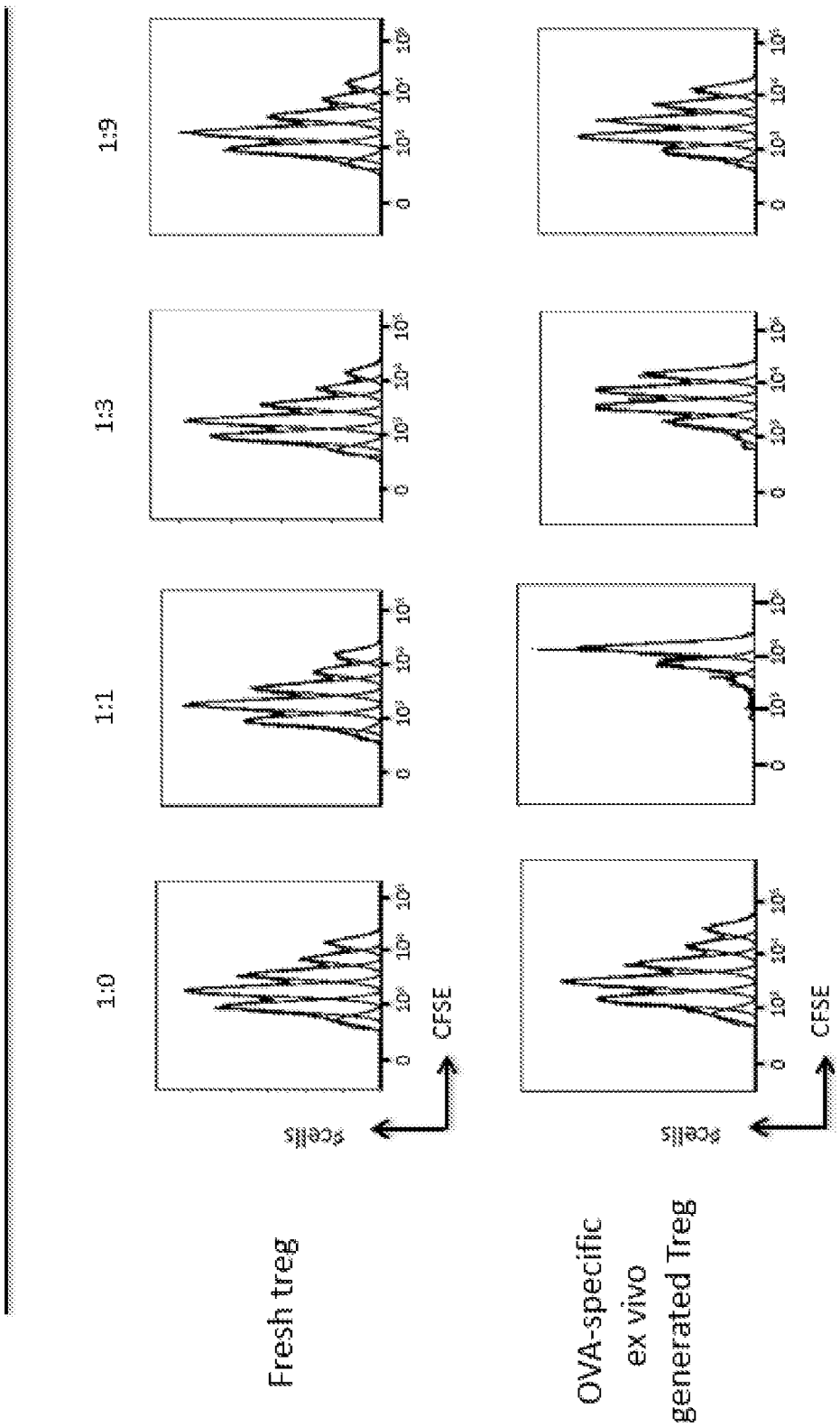
FIG. 7 (2/2)

| | T cells' origin | stimulation | medium | Stability and function in an inflammatory environment | IL1R1 expression (%) |
|---|---|---|---|---|---|
| resting Treg | Treg isolated from PBMCs | - | | NO | 27% |
| ex vivo expanded Treg | Treg isolated from PBMCs | CD3/CD28 | IL-2 | NO | 45% |
| in vitro induced Treg | Tconv isolated from PBMCs | CD3/CD28 | IL-2/TGFb/RAPA | NO | 30% |
| in vitro induced Treg | CD4+ naive T cells | CD3/CD28 | IL-2/TGFb/RAPA/PGE2 | YES | 1.7% |
| in vitro induced Treg | CD4+ naive T cells | Tolerogenic OVA pulsed imDC | IL-2/TGFb/RAPA/PGE2 | YES | 2% |

FIG. 11

EX VIVO GENERATION OF MHCII RESTRICTED CD4+ FOXP3+ REGULATORY T CELLS AND THERAPEUTIC USES THEREOF

FIELD OF INVENTION

The present invention relates to an ex vivo method for generating and expanding MHCII restricted CD4+ Foxp3+ regulatory T cells and therapeutic uses thereof.

BACKGROUND OF INVENTION

The use of regulatory T cells, either as immunogen for anti-idiotypic cancer vaccine directed to cancer cell-specific regulatory T cell subsets or in adoptive therapy for the treatment of auto-immune and allo-immune diseases, is associated with many challenges.

First, the lack of specific cellular markers for adequate purification as Foxp3 protein is not accessible because of its intra-nuclear location. The combination of CD25 and CD127 has also proved to be insufficient for isolation of pure regulatory T cells. The lack of purity is caused by contamination with effector T cells and this reduces the potency of the purified regulatory T cells.

Second, there is a need for an in vitro expansion step to generate sufficient number of cells for regulatory T cells-based cellular therapies. This external manipulation induces alteration in regulatory T cells function, resulting in loss of suppressive function and production of pro-inflammatory cytokines.

Third, the isolation of antigen-specific regulatory T cells from human peripheral blood is challenging and not practical, due to the low frequency of antigen-specific regulatory T cells in peripheral blood and the limited availability of proper peptide-MHC multimers for isolating these cells.

Therefore, there is a need for methods providing an in vitro induction of regulatory T cells from naive CD4+ T cells.

However, it has been shown that in inflammatory context, regulatory T cells can convert into TH-17 cells secreting IL-17 and IL-21 cytokines that promote tissue inflammation (Koenen et al. Blood 2008, 112 (6): 2340-2352). This is a considerable drawback for their use in cell therapy, as conversion of the regulatory T cells into TH-17 cells in vivo is undesired.

The present invention thus provides a method for ex vivo generating and expanding MHCII restricted CD4+ Foxp3+ regulatory T cells that remain stable in inflammatory condition, i.e. that do not convert into TH17 cells.

SUMMARY

The present invention relates to a method for generating ex vivo MHCII restricted CD4+ Foxp3+ regulatory T cells having the following phenotype: CD3+ CD4+ Foxp3+, comprising:
- culturing CD3+ CD4+ CD25− T cells in the presence of a TCRαβ cell activator and the following agents: i) an cAMP (Cyclic adenosine monophosphate) activator, ii) a TGFβ (Transforming growth factor beta) pathway activator, iii) a mTOR inhibitor, and optionally iv) at least one cytokine selected in the group of IL-2, IL-7, IL-15 and TSLP, for at least 5 days.

In one embodiment, the TCRαβ cell activator is a polyclonal TCRαβ cell activator, preferably an anti-CD3 antibody or an anti-TCRαβ antibody.

In one embodiment of the present invention, the αβ T cell activator is an antigen-specific TCRαβ cell activator, preferably tolerogenic dendritic cells (DCs) and pulsed with at least one self-peptide antigen.

According to one embodiment, the cAMP activator is selected from the group comprising prostaglandin E2 (PGE2), an EP2 or EP4 agonist, a membrane adenine cyclase activator or a metabotropic glutamate receptors agonist.

In one embodiment, the TGFβ pathway activator is selected from the group comprising TGFβ, bone morphogenetic proteins (BMPs), growth and differentiation factors (GDFs), anti-müllerian hormone (AMH), activin and nodal.

In one embodiment, the mTOR inhibitor is rapamycin, rapamycin analogs, wortmannin; theophylline; caffeine; epigallocatechin gallate (EGCG), curcumin, resveratrol; genistein, 3,3-diindolylmethane (DIM), LY294002 (2-(4-morpholinyl)-8-phenyl-4H-1-benzopyran-4-one), PP242, PP30, Torin1, Ku-0063794, WAY-600, WYE-687, WYE-354, GNE477, NVP-BEZ235, PI-103, XL765 and WJD008.

In one embodiment, the method according to the invention further comprises an expansion step, wherein the MHCII restricted CD4+ Foxp3+ regulatory T cells obtained by the generation method as described above are cultured in the presence of an αβ T cell activator and the following agents: i) an cAMP (Cyclic adenosine monophosphate) activator, ii) a TGFβ (Transforming growth factor beta) pathway activator, iii) a mTOR inhibitor, and optionally iv) at least one cytokine selected in the group of IL-2, IL-7, IL-15 and TSLP, for at least 5 days.

The present invention also relates to an ex vivo generated MHCII restricted CD4+ Foxp3+ regulatory T cell population obtainable by the method according to the invention.

The present invention further relates to an ex vivo generated and expanded MHCII restricted CD4+ Foxp3+ regulatory T cell population obtainable by the method according to the invention.

Another object of the present invention is an ex vivo generated MHCII restricted CD4+ Foxp3+ regulatory T cell population that remains stable in inflammatory condition.

A further object of the present invention is an immunogenic product comprising inactivated MHCII restricted CD4+ Foxp3+ regulatory T cells.

The present invention also relates to a pharmaceutical composition comprising inactivated MHCII restricted CD4+ Foxp3+ regulatory T cells and at least pharmaceutically acceptable excipient.

The present invention further relates to a vaccine composition comprising inactivated MHCII restricted CD4+ Foxp3+ regulatory T cells and at least one adjuvant.

Another object of the present invention relates to the immunogenic product, pharmaceutical composition or vaccine composition according to the invention for use in treating cancer.

A further object of the present invention is a pharmaceutical composition comprising MHCII restricted CD4+ Foxp3+ regulatory T cells and at least one pharmaceutically acceptable excipient.

The present invention also relates to a pharmaceutical composition according to the invention for use in cell therapy.

The present invention further relates to a pharmaceutical composition as described above for use in treating inflammatory or autoimmune diseases or for preventing transplant rejection or graft versus host disease (GVHD).

Definitions

As used herein, "regulatory T cells" or "Treg" refers to cells capable of suppressive activity (i.e. inhibiting proliferation of conventional T cells), either by cell-cell contact or by MLR suppression (Mixed Lymphocytes Reaction). These cells include different subpopulations including but not limited to, peripheral regulatory T cells, γδ regulatory T cells and invariant regulatory T cells.

As used herein, "invariant regulatory T cells" refers to cells having the following phenotype: $CD3^+$ $V\alpha24^+$ $Foxp3^+$. These cells recognize non peptide lipid antigens under CD1 restriction.

As used herein, "γδ regulatory T cells" refers to cells having the following phenotype: $\gamma\delta TCR^+$ $Foxp3^+$. These cells recognize non peptide phospho antigens with no MHC (major histocompatibility complex) restriction.

As used herein, "MHCII restricted $CD4^+$ $Foxp3^+$ regulatory T cells" refers to cells having the following phenotype: $CD4^+$ $CD25^+$ $Foxp3^+$. These cells are thymic derived or peripherally induced. These cells can be identified by their αβTCR (T cell receptor) and recognize peptides (including foreign or self peptides) presented by restricted MHC class II (major histocompatibility complex class II) molecules.

As used herein, the term "treatment" refers to therapeutic treatment and prophylactic and preventive measures, wherein the object is to prevent or slow down (lessen, diminish) the targeted pathological disorder or condition. Those in need of treatment include those already with the disorder as well as those prone to have the disorder or those in whom the disorder is to be prevented. A subject or mammal is successfully "treated" for a disease if, after receiving a therapeutic amount of MHCII restricted $CD4^+$ $Foxp3^+$ regulatory T cells or a therapeutically amount of inactivated MHCII restricted $CD4^+$ $Foxp3^+$ regulatory T cells according to the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

As used herein, "therapeutically effective amount" refers to the number of MHCII restricted $CD4^+$ $Foxp3^+$ regulatory T cells or of inactivated MHCII restricted $CD4^+$ $Foxp3^+$ regulatory T cells that is aimed at inducing a therapeutic response, without causing significant negative or adverse side effects to the target. A therapeutically effective amount may be administered prior to the onset of the disease to be treated, for a prophylactic or preventive action. Alternatively or additionally, the therapeutically effective amount may be administered after initiation of the disease to be treated, for a therapeutic action.

As used herein, "therapeutic response" refers to a therapeutic benefit induced by the MHCII restricted $CD4^+$ $Foxp3^+$ regulatory T cell therapy or the MHCII restricted $CD4^+$ $Foxp3^+$ regulatory T cell vaccination in a subject. A therapeutic response may include the fact of (1) delaying or preventing the onset of the disease to be treated; (2) slowing down or stopping the progression, aggravation, or deterioration of one or more symptoms of the disease to be treated; (3) bringing about ameliorations of the symptoms of the disease to be treated; (4) reducing the severity or incidence of the disease to be treated; or (5) curing the disease to be treated.

As used herein, "about" preceding a figure means more or less 10% of the value of said figure.

As used herein, "subject or patient" refers to a mammal, preferably a human. In the present invention, the terms subject and patient may be used with the same meaning. Examples of non-human mammal include a pet such as a dog, a cat, a domesticated pig, a rabbit, a ferret, a hamster, a mouse, a rat and the like; a primate such as a chimp, a monkey, and the like; an economically important animal such as cattle, a pig, a rabbit, a horse, a sheep, a goat. In one embodiment, the subject is awaiting the receipt of, or is receiving medical care or was/is/will be the object of a medical procedure, or is monitored for the development of a disease. In one embodiment, the subject is an adult (for example a subject above the age of 18). In another embodiment, the subject is a child (for example a subject below the age of 18). In one embodiment, the subject is a male. In another embodiment, the subject is a female.

As used herein, "allogeneic cells" refers to cells isolated from one subject (the donor) and infused in another (the recipient or host).

As used herein, "autologous cells" refers to cells that are isolated and infused back into the same subject (recipient or host).

DETAILED DESCRIPTION

The present invention relates to a method for generating ex vivo MHCII restricted $CD4^+$ $Foxp3^+$ regulatory T cells.

In one embodiment, the method for generating ex vivo MHCII restricted $CD4^+$ $Foxp3^+$ regulatory T cells, comprises:
culturing $CD3^+$ $CD4^+$ $CD25^-$ T cells, preferably $CD3^+$ $CD4^+$ $CD25^-$ $CD45RA^+$ T cells, in the presence of a TCRαβ activator and the following agents: i) an cAMP (Cyclic adenosine monophosphate) activator, ii) a TGFβ (Transforming growth factor beta) pathway activator, iii) a mTOR inhibitor, and optionally iv) at least one cytokine selected in the group of IL-2, IL-7, IL-15 and TSLP (Thymic stromal lymphopoietin), for at least 5 days,
thereby obtaining a population of MHCII restricted $CD4^+$ $Foxp3^+$ regulatory T cells ex vivo generated, preferably from nave ($CD45RA^+$) T cells.

In one embodiment, the $CD3^+$ $CD4^+$ $CD25^-$ T cells, preferably $CD3^+$ $CD4^+$ $CD25^-$ $CD45RA^+$ T cells, are obtained by any technic well known in the art from a blood sample. In one embodiment, the $CD3^+$ $CD4^+$ $CD25^-$ T cells, preferably $CD3^+$ $CD4^+$ $CD25^-$ $CD45RA^+$T cells, are isolated from PBMCs (peripheral blood mononuclear cells) by flow cytometry or by negative selection using a MACS system for example.

In another embodiment, the $CD3^+$ $CD4^+$ $CD25^-$ T cells, preferably $CD3^+$ $CD4^+$ $CD25^-$ $CD45RA^+$ T cells, are $CD62L^+$.

In another embodiment, the $CD3^+$ $CD4^+$ $CD25^-$ T cells, preferably $CD3^+$ $CD4^+$ $CD25^-$ $CD45RA^+$ T cells, are $CD127^+$.

In another embodiment, $CD3^+$ $CD4^+$ $CD25^-$ T cells, preferably $CD3^+$ $CD4^+$ $CD25^-$ $CD45RA^+$ T cells, are $CD27^+$.

In another embodiment, $CD3^+$ $CD4^+$ $CD25^-$ T cells, preferably $CD3^+$ $CD4^+$ $CD25^-$ $CD45RA^+$ T cells, are $IL-1R1^-$.

In another embodiment, $CD3^+$ $CD4^+$ $CD25^-$ T cells, preferably $CD3^+$ $CD4^+$ $CD25^-$ $CD45RA^+$ T cells, are $IL-6R^-$.

In another embodiment, CD3$^+$ CD4$^+$ CD25$^-$ T cells, preferably CD3$^+$ CD4$^+$ CD25$^-$ CD45RA$^+$ T cells, are IL-23R$^-$.

In another embodiment, CD3$^+$ CD4$^+$ CD25$^-$ T cells, preferably CD3$^+$ CD4$^+$ CD25$^-$ CD45RA$^+$ T cells, are IL-33R$^-$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ CD127$^+$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ CD27$^+$.

In another embodiment, the CD3$^+$ CD4$^+$ CD25$^-$ T cells, preferably CD3$^+$ CD4$^+$ CD25$^-$ CD45RA$^+$ T cells, are CD127$^+$ CD27$^+$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ IL-6R$^-$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ IL-23R$^-$.

In another embodiment, the CD3$^+$ CD4$^+$ CD25$^-$ T cells, preferably CD3$^+$ CD4$^+$ CD25$^-$ CD45RA$^+$ T cells, are CD62L$^+$ IL-33R$^-$.

In another embodiment, the CD3$^+$ CD4$^+$ CD25$^-$ T cells, preferably CD3$^+$ CD4$^+$ CD25$^-$ CD45RA$^+$ T cells, are CD127$^+$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are CD127$^+$ IL-6$^-$.

In another embodiment, the CD3$^+$ CD4$^+$ CD25$^-$ T cells, preferably CD3$^+$ CD4$^+$ CD25$^-$ CD45RA$^+$ T cells, are CD127$^+$ IL-23$^-$.

In another embodiment, the CD3$^+$ CD4$^+$ CD25$^-$ T cells, preferably CD3$^+$ CD4$^+$ CD25$^-$ CD45RA$^+$ T cells, are CD127$^+$ IL-33$^-$.

In another embodiment, the CD3$^+$ CD4$^+$ CD25$^-$ T cells, preferably CD3$^+$ CD4$^+$ CD25$^-$ CD45RA$^+$ T cells, are CD27$^+$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are CD27$^+$ IL-6$^-$.

In another embodiment, the CD3$^+$ CD4$^+$ CD25$^-$ T cells, preferably CD3$^+$ CD4$^+$ CD25$^-$ CD45RA$^+$ T cells, are CD27$^+$ IL-23$^-$.

In another embodiment, the CD3$^+$ CD4$^+$ CD25$^-$ T cells, preferably CD3$^+$ CD4$^+$ CD25$^-$ CD45RA$^+$ T cells, are CD27$^+$ IL-33$^-$.

In another embodiment, the CD3$^+$ CD4$^+$ CD25$^-$ T cells, preferably CD3$^+$ CD4$^+$ CD25$^-$ CD45RA$^+$ T cells, are IL-6$^-$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are IL-23$^-$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are IL-33$^-$ IL-1R1$^-$.

In another embodiment, the CD3$^+$ CD4$^+$ CD25$^-$ T cells, preferably CD3$^+$ CD4$^+$ CD25$^-$ CD45RA$^+$ T cells, are IL-23$^-$ IL-6$^-$.

In another embodiment, the CD3$^+$ CD4$^+$ CD25$^-$ T cells, preferably CD3$^+$ CD4$^+$ CD25$^-$ CD45RA$^+$ T cells, are IL-33$^-$ IL-6$^-$.

In another embodiment, the CD3$^+$ CD4$^+$ CD25$^-$ T cells, preferably CD3$^+$ CD4$^+$ CD25$^-$ CD45RA$^+$ T cells, are IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ CD27$^+$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ IL-6R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD27$^+$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD27$^+$ IL-6R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD27$^+$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD27$^+$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ CD27$^+$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ CD27$^+$ IL-6R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ CD27$^+$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ CD27$^+$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-6R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-23R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-33R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-6R$^-$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-6R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-6R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-23R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-33R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-6R$^-$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-6R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD127$^+$ IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-6R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-23R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-33R$^-$ IL-1R1$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-6R$^-$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-6R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD27$^+$ IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are IL-1R1$^-$ IL-6R$^-$ IL-23R$^-$.

In another embodiment, CD3$^+$ CD4$^+$ CD25$^-$ T cells, preferably CD3$^+$ CD4$^+$ CD25$^-$ CD45RA$^+$ T cells, are IL-1R1$^-$ IL-6R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are IL-6R$^-$ IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are IL-1R1$^-$ IL-6R$^-$ IL-23R$^-$ IL-33R$^-$.

In another embodiment, CD3$^+$ CD4$^+$ CD25$^-$ T cells, preferably CD3$^+$ CD4$^+$ CD25$^-$ CD45RA$^+$ T cells, are CD62L$^+$ CD127$^+$ CD27$^+$ IL-1R1$^-$ IL-6R$^-$ IL-23R$^-$ IL-33R$^-$.

In another embodiment, the CD3$^+$ CD4$^+$ CD25$^-$ T cells, preferably CD3$^+$ CD4$^+$ CD25$^-$ CD45RA$^+$ T cells, are TCRγδ$^-$.

In another embodiment, the CD3$^+$ CD4$^+$ CD25$^-$ T cells, preferably CD3$^+$ CD4$^+$ CD25$^-$ CD45RA$^+$ T cells, are Vα24$^-$.

In one embodiment, the CD3$^+$ CD4$^+$ CD25$^-$ T cells, preferably CD3$^+$ CD4$^+$ CD25$^-$ CD45RA$^+$ T cells, may be isolated from frozen PBMCs.

In one embodiment, the obtainment of isolated CD3$^+$ CD4$^+$ CD25$^-$ T cells, preferably CD3$^+$ CD4$^+$ CD25$^-$ CD45RA$^+$ T cells, may be improved by an optional first to a purification step. The CD3$^+$ CD4$^+$ CD25$^-$ T cells, preferably CD3$^+$ CD4$^+$ CD25$^-$ CD45RA$^+$ T cells, are stimulated with antigen pulsed tolerogenic DCs (for example ovalbumin pulsed tolerogenic DCs) in the presence of soluble anti-CD28 and anti-CD40 antibodies. In one embodiment, the time of stimulation ranges between 1 hour and 24 hours, preferably between 10 hours and 20 hours, more preferably during about 16 hours. After stimulation, cells are washed, for example with PBS, and stained with anti-CD154 and anti-CD4 antibodies for sorting. The purified CD3$^+$ CD4$^+$ CD25$^-$ CD154$^+$ T cells are enriched and may be used for the following activation step.

In one embodiment, the CD3$^+$ CD4$^+$ CD25$^-$ T cells are activated in the presence of an αβTCR cell activator. Said αβTCR cell activator can be a polyclonal αβTCR cell activator or an antigen-specific αβTCR cell activator.

In the present invention, the polyclonal αβTCR cell activator is a TCR αβ activator. Examples of TCR αβ activator include, but are not limited to, anti-TCR αβ antibody such as purified anti-human TCR α/β antibody (ref 306702, Biolegend), Anti-Human alpha beta TCR antibody (ref 11-9986-41, eBioscience), anti-human TCR αβ (ref 563826, BD Biosciences), TCR alpha/beta antibody (ref GTX80083, GeneTex); anti-CD3 antibody such as purified anti-human CD3 antibody (ref 344801, BioLegend), anti-CD3 antibody (ab5690, Abcam), anti-human CD3 purified (ref 14-0038-80, eBioscience), CD3 antibody (ref MA5-17043, Invitrogen antibodies), CD3 monoclonal antibody (ref ALX-804-822-C100, Enzo Life Sciences), human CD3 antibody (ref 130-098-162, Miltenyi Biotec); mitogen such as pokeweed mitogen, ionomycin, phorbol myristate acetate (PMA), phytohaemagglutinin (PHA), lipopolysaccharide (LPS), superantigen such as staphylococcal enterotoxins (SPE), retroviral antigens, streptococcal antigens, mycoplasma antigens, mycobacterium antigens, viral antigens (e.g., a superantigen from mouse mammary tumor virus, rabies virus or herpes virus) and endoparasitic antigens (e.g., protozoan or helminth antigens).

In one embodiment, the polyclonal TCRαβ cell activator is an anti-TCRαβ antibody or an anti-CD3 antibody.

In one embodiment, the polyclonal TCRαβ cell activator, preferably the anti-TCRαβ or anti-CD3 antibody, is soluble in the culture medium. In another embodiment, the polyclonal TCR αβ cell activator is coated to the culture plate.

In one embodiment, the polyclonal TCRαβ cell activator is used in the presence of feeder cells, preferably autologous feeder cells.

Feeder cells include, but are not limited to, ΔCD3 cells (T cell-depleted accessory cells), irradiated PBMCs, irradiated DCs, artificial APCs (antigen presenting cells), Sf9 cells, insect cells, a pool of PBMCs or a pool of B cells from different subjects, KCD40L cells EBV-transformed B cell lines and EBV-transformed lymphoblastoid cells (LCL).

Preferably, the feeder cells used in the invention are ΔCD3 cells that are isolated by negative selection from PBMCs by incubation with anti-CD3 coated beads and then irradiated at 3000 rad.

In one embodiment, the ratio T cells/feeder cells is from about 1:100 to about 1:10 000, preferably from 1:1 000 to 1:5 000. Within the scope of the invention, the expression "from 1:100 to 1:10 000" includes, without limitation, 1:100, 1:200, 1:300, 1:400, 1:500, 1:600, 1:700, 1:800, 1:900, 1:1 000, 1:1 250, 1:1 500, 1:1 750, 1:2 000, 1:2 250, 1:2 500, 1:2 750, 1:3 000, 1:3 250, 1:3 500, 1:3 750, 1:4 000, 1:4 250, 1:4 500, 1:4 750, 1:5 000, 1:5 250, 1:5 500, 1:5 750, 1:6 000, 1:6 250, 1:6 500, 1:6 750, 1:7 000, 1:7 250, 1:7 500, 1:7 750, 1:8 000, 1:8 250, 1:8 500, 1:8 750, 1:9 000, 1:9 250, 1:9 500, 1:9 750 and 1:10 000.

In the present invention, the antigen-specific TCRαβ cell activator is tolerogenic dendritic cells (DCs).

As used herein, "tolerogenic DCs" refers to DCs capable to induce tolerance. In one embodiment, tolerogenic DCs are capable of secreting more suppressive cytokines such as IL-10 and TGFβ than proinflammatory cytokines such as IL-12, IL-23 or TNFα. In one embodiment, DCs are defined as tolerogenic when they secrete IL-10 and IL-12 in a ratio IL-10:IL-12>1.

In one embodiment, tolerogenic DCs express on their surface the major histocompatibility (MHC) class Ia and/or MHC class Ib. The MHC class Ia presentation refers to the "classical" presentation through HLA-A, HLA-B and/or HLA-C molecules whereas the MHC class Ib presentation refers to the "non-classical" antigen presentation through HLA-E, HLA-F, HLA-G and/or HLA-H molecules.

In one embodiment, tolerogenic DCs express 50% of MHC class Ia molecules and 50% of MHC class Ib molecules on their surface. In one embodiment, tolerogenic DCs express 45% of MHC class Ia molecules and 55% of MHC class Ib molecules on their surface. In one embodiment, tolerogenic DCs express 40% of MHC class Ia molecules and 60% of MHC class Ib molecules on their surface. In one embodiment, tolerogenic DCs express 35% of MHC class Ia molecules and 65% of MHC class Ib molecules on their surface. In one embodiment, tolerogenic DCs express 30% of MHC class Ia molecules and 70% of MHC class Ib molecules on their surface. In one embodiment, tolerogenic DCs express 25% of MHC class Ia molecules and 75% of MHC class Ib molecules on their surface. In one embodiment, tolerogenic DCs express 20% of MHC class Ia molecules and 80% of MHC class Ib molecules on their surface. In one embodiment, tolerogenic DCs express 15% of MHC class Ia molecules and 85% of MHC class Ib molecules on their surface. In one embodiment, tolerogenic DCs express 10% of MHC class Ia molecules and 90% of MHC class Ib molecules on their surface. In one embodiment, tolerogenic DCs express 5% of MHC class Ia molecules and 95% of MHC class Ib molecules on their surface. In one embodiment, tolerogenic DCs express only MHC class Ib molecules on their surface.

In one embodiment, tolerogenic DCs express 50% of HLA-A, HLA-B and/or HLA-C molecules and 50% of HLA-E molecules on their surface. In one embodiment, tolerogenic DCs express 45% of HLA-A, HLA-B and/or HLA-C molecules and 55% of HLA-E molecules on their surface. In one embodiment, tolerogenic DCs express 40% of HLA-A, HLA-B and/or HLA-C molecules and 60% of HLA-E molecules on their surface. In one embodiment, tolerogenic DCs express 35% of HLA-A, HLA-B and/or HLA-C molecules and 65% of HLA-E molecules on their surface. In one embodiment, tolerogenic DCs express 30% of HLA-A, HLA-B and/or HLA-C molecules and 70% of HLA-E molecules on their surface. In one embodiment, tolerogenic DCs express 25% of HLA-A, HLA-B and/or HLA-C molecules and 75% of HLA-E molecules on their surface. In one embodiment, tolerogenic DCs express 20% of HLA-A, HLA-B and/or HLA-C molecules and 80% of HLA-E molecules on their surface. In one embodiment, tolerogenic DCs express 15% of HLA-A, HLA-B and/or HLA-C molecules and 85% of HLA-E molecules on their surface. In one embodiment, tolerogenic DCs express 10% of HLA-A, HLA-B and/or HLA-C molecules and 90% of HLA-E molecules on their surface. In one embodiment, tolerogenic DCs express 5% of HLA-A, HLA-B and/or HLA-C molecules and 95% of HLA-E molecules on their surface. In one embodiment, tolerogenic DCs express only HLA-E molecules on their surface.

Methods for obtaining tolerogenic DCs are well-known in the art. An exemplary method is the generation of tolerogenic DCs from CD14$^+$ monocytes. For example, CD14$^+$ monocytes are cultured in the presence of GM-CSF and IL-4, or in the presence of GM-CSF and IFNα, for the generation of immature DCs.

Methods for inhibiting MHC class Ia molecules expression or inducing the expression of HLA-E molecules on the surface of tolerogenic DCs are well-known.

The inhibition of the TAP transporter (transporter associated with antigen processing) leads to a decreased expression of MHC class Ia molecules thereby promoting HLA-E molecules expression on the surface of tolerogenic DCs.

Exemplary methods to inhibit the TAP transporter in the endoplasmic reticulum include, but are not limited to, CRISPR-CAS-9 technology, silencing RNA, transfected DCs with the UL-10 viral protein from the CMV (cytomegalovirus) or the use of viral proteins.

Examples of viral proteins able to inhibit the TAP transporter include, but are not limited to, HSV-1 ICP47 protein, varicella-virus UL49.5 protein, cytomegalovirus US6 protein or gammaherpesvirus EBV BNLF2a protein.

Another method is the use of a chemical product to inhibit the expression of MHC class Ia molecules without changing HLA-E expression on the surface of tolerogenic DCs. Examples of chemical products include, but are not limited to, 5'-methyl-5'-thioadenosine or leptomycin B.

The tolerogenic DCs are pulsed in the presence of at least one self-peptide antigen, modified self-peptide antigen, over-expressed self-peptide antigen or foreign antigen. By "self-peptide antigen" is meant an antigen that is normally expressed in the body from which the regulatory T cells are derived. In another embodiment, self-antigen is comparable to one, or, in another embodiment, indistinct from one normally expressed in a body from which the regulatory T cells are derived, though may not directly correspond to the antigen. In another embodiment, self-antigen refers to an antigen, which when expressed in a body, may result in the education of self-reactive T cells. In one embodiment, self-antigen is expressed in an organ that is the target of an autoimmune disease. In one embodiment, the self-antigen is expressed in a pancreas, thyroid, connective tissue, kidney, lung, digestive system or nervous system. In another embodiment, self-antigen is expressed on pancreatic β cells.

Examples of self-peptide antigen, modified self-peptide antigen and over-expressed self-peptide antigen include, but are not limited to, antigenic peptides of insulin, insulin beta, glutamic acid decarboxylase 1 (GAD1), glutamic acid decarboxylase 65 (GAD 65), HSP, thyroglobulin, nuclear proteins, acetylcholine receptor, collagen, thyroid stimulating hormone receptor (TSHR), ICA512(IA-2) and IA-21β (phogrin), carboxypeptidase H, ICA69, ICA12, thyroid peroxidase, native DNA, myelin basic protein, myelin proteolipid protein, acetylchohne receptor components, histocompatibility antigens, antigens involved in graft rejection and altered peptide ligands.

In another embodiment, the self-peptide antigen is derived from immunogenic apoptotic bodies from cancer cells or derived from tissue lysate.

Cancer cells may derive from tumor biopsy or from expansion of circulatory cancer cells.

Immunogenic apoptotic bodies from cancer cells may be obtained for example with anthracyclines including doxorubicin, daunorubicin, idarubicin and mitoxanthrone; oxaliplatin, UVC or γ-radiation treated cancer cells releasing apoptotic bodies or can be directly isolated from anthracyclines including doxorubicin, daunorubicin, idarubicin and mitoxanthrone; oxaliplatin; UVC or γ-radiation treated cancer.

Examples of tissue lysate include, but are not limited to, synovial liquid or inflammatory tissue lysate.

By "foreign antigen" is meant a molecule or molecules which is/are not endogenous or native to a mammal which is exposed to it. The foreign antigen may elicit an immune response, e.g. a humoral and/or T cell mediated response in the mammal. Generally, the foreign antigen will result in the production of antibodies there against. Examples of foreign antigens include, but are not limited to, proteins (including a modified protein such as a glycoprotein, a mucoprotein, etc.), nucleic acids, carbohydrates, proteoglycans, lipids, mucin molecules, immunogenic therapeutic agents (including proteins such as antibodies, particularly antibodies comprising non-human amino acid residues, e.g. rodent, chimeric/humanized, and primatized antibodies), toxins (optionally conjugated to a targeting molecule such as an antibody, wherein the targeting molecule may also be immunogenic), gene therapy viral vectors (such as retroviruses and adenoviruses), grafts (including antigenic components of the graft to be transplanted into the heart, lung, liver, pancreas, kidney of graft recipient and neural graft components), infectious agents (such as bacteria and virus or other organism, e.g., protists), alloantigens (i.e. an antigen that occurs in some, but not in other members of the same species) such as differences in blood types, human lymphocyte antigens (HLA), platelet antigens, antigens expressed on transplanted organs, blood components, pregnancy (Rh), and hemophilic factors (e.g. Factor VTfl and Factor IX).

In one embodiment, the self-peptide antigen or the foreign antigen is soluble.

In one embodiment, the cAMP activator added in the culture allows the activation of the cAMP pathway. Examples of cAMP activator include, but are not limited to PGE2 (prostaglandin E2), an EP2 or EP4 agonist, a membrane adenine cyclase activator such as forskolin, or metabotropic glutamate receptors agonists. Examples of PGE2 include, but are not limited to, PGE2 of ref P5640 or P0409 (Sigma-Aldrich), PGE2 of ref 2296 (R&D Systems), PGE2 of ref 2268 (BioVision), PGE2 of ref 72192 (Stemcell), PGE2 of ref ab144539 (Abcam), and PGE2 of ref 14010 (Cayman Chemical).

In one embodiment, the cAMP activator, preferably PGE2 is used at a concentration ranging from 0.01 µM to 10 µM. Within the scope of the invention, the expression "from 0.01 µM to 10 µM" includes, without limitation, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 1.5 µM, 2 µM, 2.5 µM, 3 µM, 3.5 µM, 4 µM, 4.5 µM, 5 µM, 6 µM, 7 µM, 8 µM, 9 µM. In certain embodiments, PGE2 is at a concentration ranging from 0.03 µM to 1.5 µM.

In one embodiment, the TGFβ pathway activator added in the culture allows the activation of the TGFβ pathway. Examples of TGFβ pathway activators include, but are not limited to, TGFβ family (TGFβ1, TGFβ2, TGFβ3), bone morphogenetic proteins (BMPs), growth and differentiation factors (GDFs), anti-müllerian hormone (AMH), activin, and nodal. Examples of TGFβ include, but are not limited to, TGFβ1 of ref T7039 (Sigma-Aldrich), TGFβ2 of ref T2815 (Sigma-Aldrich), TGFβ3 of ref T5425 (Sigma-Aldrich), human TGFβ1 of ref P01137 (R&D system), human TGFβ1 of ref 580702 (Biolegend), TGFβ1 of ref HZ-1011 (HumanZyme), human TGFβ1 of ref 14-8348-62 (Affymetrix eBioscience).

In one embodiment, the pathway activator is used at a concentration ranging from 1 ng/ml to 20 ng/ml. Within the scope of the invention, the expression "from 1 ng/ml to 20 ng/ml" includes, without limitation, 2 ng/ml, 2.5 ng/ml, 3 ng/ml, 3.5 ng/ml, 4 ng/ml, 4.5 ng/ml, 5 ng/ml, 5.5 ng/ml, 6 ng/ml, 6.5 ng/ml, 7 ng/ml, 7.5 ng/ml, 8 ng/ml, 8.5 ng/ml, 9 ng/ml, 9.5 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml. In certain embodiments, TGFβ is at a concentration ranging from 2.5 ng/ml to 7.5 ng/ml.

In one embodiment, the mTOR inhibitor added in the culture allows the inhibition of the mTOR pathway. Examples of mTOR inhibitor include, but are not limited to, rapamycin (also named sirolimus) and its analogs (termed rapalogs); wortmannin;

theophylline; caffeine; epigallocatechin gallate (EGCG); curcumin; resveratrol; genistein; 3,3-diindolylmethane (DIM); LY294002 (2-(4-morpholinyl)-8-phenyl-4H-1-benzopyran-4-one); PP242; PP30; Torin1; Ku-0063794; WAY-600; WYE-687; WYE-354; and mTOR and PI3K dual-specificity inhibitors such as GNE477, NVP-BEZ235, PI-103, XL765 and WJD008. Examples of rapamycin include, but are not limited to, rapamycin of ref R0395 (Sigma-Aldrich), rapamycin of ref S1039 (Selleckchem), rapamycin of ref 1292 (Tocris), rapamycin of ref R-5000 (LC Laboratories), rapamycin of ref tlrl-rap (InvivoGen), rapamycin of ref ab120224 (Abcam), rapamycin of ref R0395 (Sigma-Aldrich).

Examples of compounds of the same chemical class than rapamycin used clinically include, but are not limited to, Everolimus (code name RAD001), Temsirolimus (code name CCI-779, NSC 683864), Zotarolimus (code name ABT-578).

In one embodiment, the mTOR inhibitor, preferably rapamycin, is used at a concentration ranging from 0.1 nM to 50 nM. Within the scope of the invention, the expression "from 0.1 nM to 50 nM" includes, without limitation, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM. In one embodiment, at least one cytokine selected from IL-2, IL-7, IL-15 and TSLP can be added in the culture.

In one embodiment, IL-2 is used at a concentration ranging from 10 IU/ml to 1000 IU/ml. Within the scope of the invention, the expression "from 10 IU/ml to 1000 IU/ml" includes, without limitation, 15 IU/ml, 20 IU/ml, 25 IU/ml, 30 IU/ml, 35 IU/ml, 40 IU/ml, 45 IU/ml, 50 IU/ml, 55 IU/ml, 60 IU/ml, 65 IU/ml, 70 IU/ml, 75 IU/ml, 80 IU/ml, 85 IU/ml, 90 IU/ml, 95 IU/ml, 100 IU/ml, 150 IU/ml, 200 IU/ml, 250 IU/ml, 300 IU/ml, 350 IU/ml, 400 IU/ml, 450 IU/ml, 500 IU/ml, 550 IU/ml, 600 IU/ml, 650 IU/ml, 700 IU/ml, 750 IU/ml, 800 IU/ml, 850 IU/ml, 900 IU/ml, 950 IU/ml. In certain embodiments, IL-2 is used at a concentration ranging from 50 IU/ml to 250 IU/ml.

In one embodiment, IL-7 is used at a concentration ranging from 1 ng/ml to 100 ng/ml. Within the scope of the invention, the expression "from 1 ng/ml to 100 ng/ml" includes, without limitation, 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml.

In one embodiment, IL-15 is used at a concentration ranging from 1 ng/ml to 50 ng/ml. Within the scope of the invention, the expression "from 1 ng/ml to 50 ng/ml" includes, without limitation, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 ng/ml, 40 ng/ml, 45 ng/ml. In certain embodiments, IL-15 is used at a concentration ranging from 10 ng/ml to 30 ng/ml.

In one embodiment, TSLP is used at a concentration ranging from 1 ng/ml to 100 ng/ml. Within the scope of the invention, the expression "from 1 ng/ml to 100 ng/ml" includes, without limitation, 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml.

In one embodiment neutralizing antibodies can be added to the culture to prevent the generation of other populations of regulatory T cells.

Examples of neutralizing antibodies include, but are not limited to, anti-IFNγ, anti-IL-4, and/or anti-IL-12 antibodies.

Examples of anti-IFNγ antibodies include, but are not limited to, Affymetrix eBioscience (Ref 14-7318), R&D systems (Ref MAB285), Novus Biologicals (Ref AF-485-NA).

Examples of anti-IL-γ antibodies include, but are not limited to, R&D Systems (Ref MAB304, MAB204, or MAB204), Affymetrix eBioscience (Ref 14-7048), GeneTex (Ref GTX10755).

Examples of anti-IL-12 antibodies include, but are not limited to, Affymetrix eBioscience (Ref 16-7129 or 16-8126), Biolegend (Ref 508803), R&D systems (Ref MAB219, AF-219, or AB-219).

In one embodiment, the culture medium used in the culture of the invention comprises (i) one or more pH buffering system(s); (ii) inorganic salt(s); (iii) trace element(s); (iv) free amino acid(s); (v) vitamin(s); (vi) hormone(s); (vii) carbon/energy source(s).

Examples of inorganic salts include, but are not limited to, calcium bromide, calcium chloride, calcium phosphate, calcium nitrate, calcium nitrite, calcium sulphate, magnesium bromide, magnesium chloride, magnesium sulphate, potassium bicarbonate, potassium bromide, potassium chloride, potassium dihydrogen phosphate, potassium disulphate, dipotassium hydrogen phosphate, potassium nitrate, potassium nitrite, potassium sulphite, potassium sulphate, sodium bicarbonate, sodium bromide, sodium chloride, sodium disulphate, sodium hydrogen carbonate, sodium dihydrogen phosphate, di-sodium hydrogen phosphate, sodium sulphate and a mix thereof.

Examples of trace elements include, but are not limited to, cobalt (Co), copper (Cu), iron (Fe), magnesium (Mg), manganese (Mn), molybdenum (Mo), nickel (Ni), selenium (Se), zinc (Zn) and the salts thereof.

Examples of free amino acids include, but are not limited to, L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-phenylalanine, L-proline, L-serine, taurine, L-threonine, L-tryptophan, L-tyrosine, L-valine and a mix thereof.

Examples of vitamins include, but are not limited to, biotin (vitamin H); D-calcium-pantothenate; choline chloride; folic acid (vitamin B9); myo-inositol; nicotinamide; pyridoxal (vitamin B6); riboflavin (vitamin B2); thiamine (vitamin B1); cobalamin (vitamin B12); acid ascorbic; α-tocopherol (vitamin E) and a mix thereof.

Examples of carbon/energy sources include, but are not limited to, D-glucose; pyruvate; lactate; ATP; creatine; creatine phosphate; and a mix thereof.

In one embodiment, the culture medium is a commercially available cell culture medium, in particular selected in a group comprising the IMDM (Iscove's Modified Dulbecco's Medium) from GIBCO® or the RPMI 1640 medium from GIBCO®.

In another embodiment, the culture medium is a serum-free culture medium such as the AIM-V medium from GIBCO®, the X-VIVO 10, 15 and 20 media from LONZA.

In another embodiment, the culture medium can be further supplemented with additional compound(s), in particular selected in a group comprising foetal bovine serum, pooled human AB serum, cytokines and growth factors; antibiotic(s), in particular selected in a group comprising penicillin, streptomycin and a mix thereof.

In one embodiment, the culture medium is IMDM.

In some particular embodiments, the culture medium comprises IMDM cell culture medium; from 1% (w/w) to 5% (w/w) of foetal bovine serum; from 10 IU/ml to 200 IU/ml of penicillin; from 10 IU/ml to 200 IU/ml of streptomycin; from 0.1 mM to 10 mM of a mixture of non-essential amino acids, in particular amino acids selected in a group comprising alanine, asparagine, aspartic acid, cysteine, glutamic acid, glutamine, glycine, proline, serine, and tyrosine; from 0.5 mM to 10 mM of glutamine from 10 mM to 25 mM of HEPES pH 7.6-7.8.

In one embodiment, the culture for generating the MHCII restricted CD4$^+$ Foxp3$^+$ regulatory T cells of the invention is performed during at least 5 days, at least 6 days, at least 7 days, at least 8 days. Within the scope of the invention, the expression "at least 5 days" includes, without limitation, 5 days, 6 days, 7 days, 8 days, 9 days, 10 days, 11 days, 12 days, 13 days, 14 days, 15 days.

In one embodiment, a portion of the culture medium is discarded once, twice, three times, four times or five times during the time course of the generation culture and replaced with the same volume of fresh culture medium. Within the scope of the invention the term "portion" is intended to mean at least 20% (v/v), at least 25% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v) of the volume of the culture medium. In certain embodiments, 40% (v/v) to 60% (v/v) of the volume of the culture medium of step a) is discarded. In certain embodiments, the volume that is discarded is replaced with an identical volume of fresh culture medium. Within the scope of the invention, the expression "fresh culture medium" refers to a culture medium that has not been in contact with any CD3+ T cells.

In one embodiment, the medium is a nTreg polarizing medium. The inventors define a "nTreg polarizing medium" as a medium such as RPMI medium comprising at least one cAMP activator as described hereabove, at least one TGFβ pathway activator as described here above and at least one mTor inhibitor as described hereabove. In a preferred embodiment, the "nTreg polarizing medium" refers to a RPMI medium comprising TGFβ, rapamycin and PGE2.

In another embodiment, the medium is an inflammatory medium. The inventors define an "inflammatory medium" as a medium such as IMDM comprising inflammatory cytokines such as for example IL-1β (10 ng/ml), IL-6 (30 ng/ml), IL-21 (50 ng/ml), IL-23 (30 ng/ml), IL-2 (100 UI/ml).

In one embodiment, the method for generating ex vivo MHCII restricted CD4$^+$ Foxp3$^+$ regulatory T cells, comprises:
  culturing CD3$^+$ CD4$^+$ CD25$^-$ T cells in the presence of autologous ΔCD3 feeder cells and coated anti-CD3 antibody and in the presence of the following agents: i)

PGE2, ii) TGFβ, iii) rapamycin and optionally iv) at least one cytokine selected in the group of IL-2 and IL-15, for at least 5 days, thereby obtaining a population of MHCII restricted CD4$^+$ Foxp3$^+$ regulatory T cells ex vivo generated.

In one embodiment, the method for generating ex vivo MHCII restricted CD4$^+$ Foxp3$^+$ regulatory T cells, comprises:

culturing CD3$^+$ CD4$^+$ CD25$^-$ T cells in the presence of tolerogenic DC that have been pulsed with at least one self-peptide antigen during about 24 h and in the presence of ΔCD3 feeder cells and in the presence of the following agents: i) PGE2, ii) TGFβ, iii) rapamycin and optionally iv) at least one cytokine selected in the group of IL-2 and IL-15, for at least 5 days, thereby obtaining a population of MHCII restricted CD4$^+$ Foxp3$^+$ regulatory T cells.

The present invention also relates to an ex vivo method of generation and expansion of MHCII restricted CD4$^+$ Foxp3$^+$ regulatory T cells, comprising:

generating the MHCII restricted CD4$^+$ Foxp3$^+$ regulatory T cells as described here above, expanding the MHCII restricted CD4$^+$ Foxp3$^+$ regulatory T cells generated by contacting them in the presence of an TCRαβ cell activator (preferably either autologous ΔCD3 feeder cells and coated anti-CD3 antibody or tolerogenic DC that have been pulsed with at least one self-peptide antigen during about 24 h and in the presence of ΔCD3 feeder cells) and the following agents: i) an cAMP (Cyclic adenosine monophosphate) activator (preferably PGE2), ii) a TGFβ (Transforming growth factor beta) pathway activator (preferably TGFβ), iii) a mTOR inhibitor (preferably rapamycin), and optionally iv) at least one cytokine selected in the group of IL-2, IL-7, IL-15 and TSLP (preferably IL-2 and/or IL-15), for at least 5 days, thereby obtaining an expanded population of MHCII restricted CD4$^+$ Foxp3$^+$ regulatory T cells.

In one embodiment, the MHCII restricted CD4$^+$ Foxp3$^+$ regulatory T cell population generated ex vivo is isolated by flow cytometry based on the following phenotype: CD3$^+$ TCRαβ$^+$ CD45RO$^+$ Foxp3$^+$.

In one embodiment, the isolated MHCII restricted CD4$^+$ Foxp3$^+$ regulatory T cell population thus obtained is then expanded ex vivo by culturing these cells in the presence of a polyclonal T cell activator. Examples of polyclonal αβ T cell activator are listed hereinabove. Alternatively, other examples of polyclonal αβ T cell activators that may be used during expansion include, but are not limited to, mitogen such as PMA/ionomycin, super-antigen, anti-CD3 antibody. . . . Preferably, the anti-CD3 monoclonal antibody is coated. In one embodiment, the polyclonal αβ T cell activator can be used in the presence of feeder cells as described here above.

In another embodiment, the isolated MHCII restricted CD4$^+$ Foxp3$^+$ regulatory T cell population thus obtained is then expanded ex vivo by culturing these cells in the presence of antigen-specific TCRαβ cell activator as described here above. In one embodiment, the antigen-specific TCRαβ cell activator can be used in the presence of feeder cells as described here above.

In one embodiment, the culture for expanding the ex vivo generated MHCII restricted CD4$^+$ Foxp3$^+$ regulatory T cells of the invention is performed during at least 5 days, at least 6 days, at least 7 days, at least 8 days. Within the scope of the invention, the expression "at least 5 days" includes, without limitation, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more.

In one embodiment, a portion of the culture medium is discarded once, twice, three times, four times or five times during the time course of the generation culture and replaced with the same volume of fresh culture medium. Within the scope of the invention the term "portion" is intended to mean at least 20% (v/v), at least 25% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v) of the volume of the culture medium. In certain embodiments, 40% (v/v) to 60% (v/v) of the volume of the culture medium of the first step is discarded. In certain embodiments, the volume that is discarded is replaced with an identical volume of fresh culture medium. Within the scope of the invention, the expression "fresh culture medium" refers to a culture medium that has not been in contact with any CD3+ T cells.

In one embodiment, MHCII restricted CD4$^+$ Foxp3$^+$ regulatory T cells are generated ex vivo by culturing CD3$^+$ TCR αβ$^+$ CD45RA$^+$, preferably CD3$^+$ TCR αβ$^+$ CD45RA$^+$ CD25$^-$, T cells obtained from PBMCs by negative selection (5.10$^3$ cells/ml) in the presence of autologous ΔCD3 feeder cells (125 10$^5$ cells/ml) and coated anti-CD3 antibody (2 μg/ml) in the presence of PGE2 (1 μM), TGFβ (5 ng/ml), Rapamycin (10 nM) and IL-2 (100 UI/ml) in IMDM-5. On day 1, IL-2 (100 UI/ml) and IL-15 (10 ng/ml) are added to the culture. Every 3 days, half of the medium volume is discarded and replaced by fresh medium comprising PGE2 (50 nM), TGFβ (5 ng/ml), Rapamycin (1 nM), IL-2 (100 UI/ml) and IL-15 (10 ng/ml). Once cells begin to expand, they can be split every 2 or 3 days and cultured in the presence of ΔCD3 feeder cells and coated anti-CD3 antibody every 9 days in a medium comprising PGE2 (1 μM), TGFβ (5 ng/ml), Rapamycin (10 nM) and IL-2 (100 UI/ml).

In another embodiment, MHCII restricted CD4$^+$ Foxp3$^+$ regulatory T cells are generated ex vivo by culturing CD3$^+$ TCR αβ$^+$ CD45RA$^+$ T cells, preferably CD3$^+$ TCR αβ$^+$ CD45RA$^+$ CD25$^-$, obtained from PBMCs by negative selection (5.10$^3$ cells/ml) in the presence of tolerogenic DCs, that have been pulsed with at least one self-peptide antigen during about 24 h, and in the presence of ΔCD3 feeder cells (125 10$^5$ cells/ml), PGE2 (1 μM), TGFβ (5 ng/ml), Rapamycin (10 nM) and IL-2 (100 UI/ml) in IMDM-5. On day 1, IL-2 (100 UI/ml), IL-15 (10 ng/ml) and TGFβ (5 ng/ml), are added to the culture. Every 3 days, half of the medium volume is discarded and replaced by fresh medium comprising PGE2 (50 nM), TGFβ (5 ng/ml), Rapamycin (1 nM), IL-2 (100 UI/ml) and IL-15 (10 ng/ml). Once cells begin to expand, they can be split every 2 or 3 days and restimulated every 9 days with tolerogenic DCs in the presence of ΔCD3 feeder cells and PGE2 (1 μM), TGFβ (5 ng/ml), Rapamycin (10 nM) and IL-2 (100 UI/ml).

In this embodiment, tolerogenic DCs were obtained by culturing CD14$^+$ monocytes isolated from PBMCs in the presence of AIMV supplemented with GMCSF (100 ng/ml) and IL-4 (10 ng/ml). At day 3 and 6, the medium is discarded and replaced by fresh medium comprising GM-CSF and IL-4. On day 6, the tolerogenic DCs are pulsed for 24 hours in the presence of self-peptide antigen.

The present invention also relates to MHCII restricted CD4$^+$ Foxp3$^+$ regulatory T cells obtainable by the ex vivo generation method as described here above.

The present invention also relates to MHCII restricted CD4+ Foxp3+ regulatory T cells obtainable by the ex vivo generation and expansion method as described here above.

In one embodiment, the population of MHCII restricted CD4+ Foxp3+ regulatory T cells obtained by the generation and expansion method of the invention comprises at least $10^6$, $10^7$, $10^8$, $10^9$, $10^{10}$ cells.

In one embodiment, the population of MHCII restricted CD4+ Foxp3+ regulatory T cells obtained by the generation and expansion method of the invention has the following phenotype: CD3+ TCRαβ+ Foxp3+.

In one embodiment, said population of MHCII restricted CD4+ Foxp3+ regulatory T cells has the following phenotype: CD4+ Foxp3+ CD25+.

In one embodiment, said population of MHCII restricted CD4+ Foxp3+ regulatory T cells has the following phenotype: CD4+ Foxp3+ CTLA4+.

In one embodiment, said population of MHCII restricted CD4+ Foxp3+ regulatory T cells has the following phenotype: CD4+ Foxp3+ CD45RO+.

In one embodiment, said population of MHCII restricted CD4+ Foxp3+ regulatory T cells has the following phenotype: CD4+ Foxp3+ CD25+ CTLA4+.

In one embodiment, said population of MHCII restricted CD4+ Foxp3+ regulatory T cells has the following phenotype: CD4+ Foxp3+ CD25+ CD45RO+.

In one embodiment, said population of MHCII restricted CD4+ Foxp3+ regulatory T cells has the following phenotype: CD4+ Foxp3+ CTLA4+ CD45RO+.

In one embodiment, said population of MHCII restricted CD4+ Foxp3+ regulatory T cells has the following phenotype: CD4+ Foxp3+ CD25+ CTLA4+ CD45RO+ CD127-.

In one embodiment, the MHCII restricted CD4+ Foxp3+ regulatory T cells of the invention do not present a regulatory T cells specific demethylated region (TSDR) of the gene Foxp3. In one embodiment, the MHCII restricted CD4+ Foxp3+ regulatory T cells of the invention present a regulatory T cells specific demethylated region (TSDR) of the gene Foxp3. In one embodiment, the MHCII restricted CD4+ Foxp3+ regulatory T cells present a percentage of demethylation of the TSDR of the gene FOXP3 superior to at least 30%, 40%, 50%. A protocol for measuring promoter demethylation percentage is shown in the Material and Method part of the Examples.

In another embodiment, the MHCII restricted CD4+ Foxp3+ regulatory T cells of the invention present a percentage of enrichment of acetylated histone in Foxp3 promoter region superior to at least 10%, 20%, 30%, 40% or 50%. A protocol for measuring enrichment of acetylated histones in percentage is shown in the Material and Method part of the Examples.

An example of phenotypic characteristics of the population of MHCII restricted CD4+ Foxp3+ regulatory T cells of the invention is shown in FIG. 1.

In one embodiment, said population of MHCII restricted CD4+ Foxp3+ regulatory T cells express Foxp3 with a median fluorescence intensity (MFI) at least equivalent to the Foxp3 MFI measured in nave regulatory T cells. As used herein, "nave regulatory T cells" refer to T cells having for phenotype Foxp3+ CD45RA+ CD4+ CD25+ CD127-.

In one embodiment, the MHCII restricted CD4+ Foxp3+ regulatory T cells express Foxp3 with a median fluorescence intensity (MFI) of at least 2000.

In one embodiment, the MHCII restricted CD4+ Foxp3+ regulatory T cells express Foxp3 with a median fluorescence intensity (MFI) of at least 2 or 3 fold the Foxp3 MFI measured in nave regulatory T cells.

In one embodiment, the MHCII restricted CD4+ Foxp3+ regulatory T cells express Foxp3 with a median fluorescence intensity (MFI) of at least 2000, 3000, 4000, 5000, 10000, 20000, 30000, 40000, 50000, 60000, 70000.

In one embodiment, the MHCII restricted CD4+ Foxp3+ regulatory T cells population comprises at least 65% of the CD3+ CD4+ cells expressing Foxp3. The expression "at least 65%" includes, without limitation, 65%, 66%, 67%, 68%, 69%, 70%, 71%, 72%, 73%, 74%, 752%, 76%, 77%, 78%, 79%, 80%, 81%, 82%, 83%, 84%, 85%, 86%, 87%, 88%, 89%, 90%, 91%, 82%, 93%, 94%, 95%, 96%, 97%, 98%, 99% and 100%.

As used herein, the term "expression" may refer alternatively to the transcription of a molecule (i.e. expression of the mRNA) or to the translation (i.e. expression of the protein) of a molecule. In one embodiment, detecting the expression may correspond to an intracellular detection. In another embodiment, detecting the expression may correspond to a surface detection, i.e. to the detection of molecule expressed at the cell surface. In another embodiment, detecting the expression may correspond to an extracellular detection, i.e. to the detection of secretion. In another embodiment, detecting the expression may correspond to intracellular, surface and/or extracellular detections. Methods for determining the expression level are well-known from the skilled artisan, and include, without limitation, determining the transcriptome (in an embodiment wherein expression relates to transcription of a molecule) or proteome (in an embodiment wherein expression relates to translation of a cytotoxic molecule) of cells.

In one embodiment of the invention, the expression of the molecules is assessed at the mRNA level. Methods for assessing the transcription level of a molecule are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like. In another embodiment of the invention, the expression of the molecules is assessed at the protein level. Methods for determining a protein level in a sample are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In another embodiment, determining the expression level of at least one molecule corresponds to detecting and/or quantifying binding of a ligand to a molecule. In one embodiment, said ligand is an antibody specific of said molecule, and the method of the invention comprises detecting and/or quantifying a complex formed between said antibody and said molecule. The complex can be detected if the ligand has been for example, but not limited to, covalently coupled with a detectable molecule such as an antibody constant fragment (Fc) or a fluorescent compound (e.g. Cyanine dye, Alexa dye, Quantum dye, etc). The complex can also be detected if the ligand has been tagged with different means well known to the person skilled in the art. For example, but without limitation, a tag used with the invention can be a tag selected from the group comprising or consisting of Hemaglutinin Tag, Poly Arginine Tag, Poly Histidine Tag, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. The use of the ligand therefore allows on the one hand the identification and detection of the molecule depending on the ligand used, and on the other hand the quantification of the complex formed.

In one embodiment, determining the expression level of molecules is conducted by flow cytometry, immunofluorescence or image analysis, for example high content analysis. Preferably, the determination of the expression level of molecules is conducted by flow cytometry. In one embodiment, before conducting flow cytometry analysis, cells are fixed and permeabilized, thereby allowing detecting intracellular proteins.

In one embodiment, determining the expression level of a molecule in a cell population comprises determining the percentage of cells of the cell population expressing the molecule (i.e. cells "+" for the molecule). Preferably, said percentage of cells expressing the molecule is measured by FACS.

The terms "expressing (or +)" and "not expressing (or −)" are well known in the art and refer to the expression level of the cell marker of interest, in that the expression level of the cell marker corresponding to "+" is high or intermediate, also referred as "+/−". The cell marker corresponding to "−" is a null expression level of the cell marker or also refers to less than 10% of a cell population expressing the said cell marker.

The expression level of the cell marker of interest is determined by comparing the Median Fluorescence Intensity (MFI) of the cells from the cell population stained with fluorescently labeled antibody specific for this marker to the fluorescence intensity (FI) of the cells from the same cell population stained with fluorescently labeled antibody with an irrelevant specificity but with the same isotype, the same fluorescent probe and originated from the same specie (referred as Isotype control). The cells from the population stained with fluorescently labeled antibody specific for this marker and that show equivalent MFI or a lower MFI than the cells stained with the isotype controls are not expressing this marker and then are designated (−) or negative. The cells from the population stained with fluorescently labeled antibody specific for this marker and that show a MFI value superior to the cells stained with the isotype controls are expressing this marker and then are designated (+) or positive.

In one embodiment, the MHCII restricted CD4$^+$ Foxp3$^+$ regulatory T cells are capable of suppressive activity similar to the suppressive activity of nave CD4$^+$ CD25$^+$ CD45RA$^+$ CD127$^-$ regulatory T cells. Determination of the suppressive activity of a cell population is well known in the art and can be performed by conventional assays such as the standard polyclonal cell-cell contact Treg suppression assay or the autologous MLR suppression assay as described in the Examples.

Another object of the invention is a population of MHCII restricted CD4$^+$ Foxp3$^+$ regulatory T cells that remains stable when placed in inflammatory conditions.

In one embodiment, said population of MHCII restricted CD4$^+$ Foxp3$^+$ regulatory T cells remains stable when placed in inflammatory conditions.

As used herein, "stable" refers to no secretion or a low secretion of IL-17, i.e. inferior to 200 ng/ml, 100 ng/ml, 50 ng/ml and still capable of suppressive capacity, i.e. inhibiting proliferation of conventional T cells as shown in the Examples.

As used herein, "inflammatory condition" refers to a medium enriched in aromatic acid, preferably in tryptophan, such as for example IMDM, comprising inflammatory cytokines such as for example IL-1β (10 ng/ml), IL-6 (30 ng/ml), IL-21 (50 ng/ml), IL-23 (30 ng/ml), IL-2 (100 UI/ml). A method for determining if a population of regulatory T cells remains stable in inflammatory condition comprises culturing the regulatory T cells in the inflammatory condition medium as described here above in the presence of anti-CD3 (4 μg/ml), preferably coated, and anti-CD28 (4 μg/ml), preferably in a soluble form. After 36 h to 72 h of culture, the presence of IL-17 in the culture supernatant is measured. The recognition of IL-17 in the culture supernatant may be carried out by conventional methods known in the art such as, for example, a sandwich ELISA anti-IL-17. Briefly, after coated the plate with a capture anti-IL-17 antibody, the culture supernatant is added to each well with a dilution series. After incubation, a detection anti-IL-17 antibody is added to each well. The ELISA is developed by any colorimetric means known in the art such as, for example, using detection antibody labelled with biotin, a poly-streptavidin HRP amplification system and an o-phenylenediamine dihydrochloride substrate solution. An IL-17 level inferior to 200 ng/ml, 100 ng/ml, 50 ng/ml corresponds to no secretion or low secretion of IL-17.

Without wishing to be bound to a theory, the inventors state that the stroma of malignant tumor cells comprises TILs (Tumor-infiltrating lymphocytes) that are highly enriched in regulatory T cells and that exert an immune suppressive activity, in particular on NK cells, which likely accounts on the local cancer immune escape. The inactivated MHCII restricted CD4$^+$ Foxp3$^+$ regulatory T cells may represent an antigenic target to induce an immune response directed against the MHCII restricted CD4$^+$ Foxp3$^+$ regulatory T cells present in the TILs, thereby preventing their immune suppressive activity and allowing the cytotoxic activity of effector cells such as NK cells against the tumor cells. The inventors thus suggest using a vaccine composition comprising inactivated MHCII restricted CD4$^+$ Foxp3$^+$ regulatory T cells as active principle.

One object of the invention is an immunogenic product comprising, consisting essentially of or consisting of inactivated MHCII restricted CD4$^+$ Foxp3$^+$ regulatory T cells as described here above.

In one embodiment, the immunogenic product comprises, consists essentially of or consists of inactivated MHCII restricted CD4$^+$ Foxp3$^+$ regulatory T cells having the following phenotype CD3$^+$ CD4$^+$ Foxp3$^+$ as described here above.

As used herein, the term "consisting essentially of", with reference to an immunogenic product, pharmaceutical composition, vaccine or medicament, means that the at least one MHCII restricted CD4$^+$ Foxp3$^+$ regulatory T cell population or antibody of the invention is the only one therapeutic agent or agent with a biologic activity within said immunogenic product, pharmaceutical composition, vaccine or medicament.

In one embodiment, the immunogenic product comprises, consists essentially of or consists of inactivated MHCII restricted CD4$^+$ Foxp3$^+$ regulatory T cells having the following phenotype CD3$^+$ CD4$^+$ Foxp3$^+$ generated and optionally expanded ex vivo by the method as described here above.

Another object of the invention is a pharmaceutical composition comprising, consisting essentially of or consisting of the immunogenic product as described here above and at least one pharmaceutically acceptable excipient.

Another object of the invention is a pharmaceutical composition comprising, consisting essentially of or consisting of inactivated MHCII restricted CD4$^+$ Foxp3$^+$ regulatory T cells having the following phenotype CD3$^+$ CD4$^+$ Foxp3$^+$ and at least one pharmaceutically acceptable excipient.

Another object of the invention is a pharmaceutical composition comprising, consisting essentially of or consisting of inactivated MHCII restricted CD4$^+$ Foxp3$^+$ regulatory T cells having the following phenotype CD3$^+$ CD4$^+$ Foxp3$^+$ generated and expanded ex vivo by the method as described here above and at least one pharmaceutically acceptable excipient.

As used herein, the term "excipient" refers to any and all conventional solvents, dispersion media, fillers, solid carriers, aqueous solutions, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

By "pharmaceutically acceptable" is meant that the ingredients of a pharmaceutical composition are compatible with each other and not deleterious to the subject to which it is administered. Examples of pharmaceutically acceptable excipient include, but are not limited to, water, saline, phosphate buffered saline, dextrose, glycerol, ethanol and the like or combinations thereof.

Another object of the invention is a vaccine composition comprising, consisting essentially of or consisting of the immunogenic product as described here above.

Another object of the invention is a vaccine composition comprising, consisting essentially of or consisting of inactivated MHCII restricted CD4$^+$ Foxp3$^+$ regulatory T cells having the following phenotype CD3$^+$ CD4$^+$ Foxp3$^+$.

Another object of the invention is a vaccine composition comprising, consisting essentially of or consisting of inactivated MHCII restricted CD4$^+$ Foxp3$^+$ regulatory T cells having the following phenotype CD3$^+$ CD4$^+$ Foxp3$^+$ generated and expanded ex vivo by the method as described here above.

As used herein, "inactivated" T cells refers to T cells that are viable but has reduced or no effector function, i.e. have lost any pathogenic potential. Examples of cell surface markers of inactivated T cells include, but are not limited to, 7-Aminoactinomycin D (7-AAD), calreticulin and heat shock protein 90 (HSP-90). Therefore, inactivated T cells express 7-AAD and/or calreticulin and/or HSP-90. The inactivated MHCII restricted CD4$^+$ Foxp3$^+$ regulatory T cells of the invention have lost their suppressive activity but are still immunogenic. An example of T cell effector function assay is, but not limited to, T-cell proliferation assay. T-cell proliferation may be assessed on fixed T cells versus non-fixed T cells. Briefly, the T-cell proliferation assay aims at determining the percentage of living proliferating cells in fixed versus non-fixed T cells by flow cytometry. After staining the T cells with CFSE, anti-CD3 antibody and 7-AAD, the living proliferating cells are defined as the CFSE$^{low}$ fraction in gated CD3$^+$ 7-AAD$^-$ cells.

In one embodiment, the MHCII restricted CD4$^+$ Foxp3$^+$ regulatory T cells are inactivated by any method well-known in the art. Examples of method for inactivating cells include, but are not limited to, irradiation, preferably with about 2500 to 3000 rads and/or chemical inactivation such as exposure to cisplatin, carboplatin, oxaliplatin, mitomycine C or antracycline.

In one embodiment, the vaccine composition of the invention further comprises at least one adjuvant. Examples of adjuvant that can be used in the vaccine composition include, but are not limited to, ISA51; emulsions such as CFA, MF59, montanide, AS03 and AF03; mineral salts such as alum, calcium phosphate, iron salt, zirconium salt, and AS04; TLR ligands such as TLR2 ligands (such as outersurface protein A or OspA), TLR3 ligands (such as poly I:C), TLR4 ligands (such as MPL and GLA), TLR5 ligands, TLR7/8 ligands (such as imiquimod), TLR9 ligands (such as CpG ODN); polysaccharides such as chitin, chitosan, α-glucans, β-glucans, fructans, mannans, dextrans, lentinans, inulin-based adjuvants (such as gamma inulin); TLR9 and STING ligands such as K3 CpG and cGAMP. As used herein, "adjuvant" refers to an agent that potentiates the immune responses to an antigen and/or modulates it towards the desired immune responses.

In one embodiment, the inactivated MHCII restricted CD4$^+$ Foxp3$^+$ regulatory T cells are specific of at least one self-peptide antigen as described hereabove.

In another embodiment, the inactivated MHCII restricted CD4$^+$ Foxp3$^+$ regulatory T cells are specific of at least one self-peptide antigen that were present on apoptotic bodies of cancer cells.

In one embodiment, the inactivated MHCII restricted CD4$^+$ Foxp3$^+$ regulatory T cells present in the immunogenic product, pharmaceutical composition or vaccine composition of the invention are human MHCII restricted CD4$^+$ Foxp3$^+$ regulatory T cells.

In one embodiment, the inactivated MHCII restricted CD4$^+$ Foxp3$^+$ regulatory T cells present in the immunogenic product, pharmaceutical composition or vaccine composition of the invention are autologous MHCII restricted CD4$^+$ Foxp3$^+$ regulatory T cells.

In one embodiment, the inactivated MHCII restricted CD4$^+$ Foxp3$^+$ regulatory T cells present in the immunogenic product, pharmaceutical composition or vaccine composition of the invention are allogenic MHCII restricted CD4$^+$ Foxp3$^+$ regulatory T cells.

In another embodiment, the immunogenic product, pharmaceutical composition or vaccine composition of the invention may be personalized for a patient. As used herein, a "personalized" immunogenic product or vaccine composition refers to the use of MHCII restricted CD4$^+$ Foxp3$^+$ regulatory T cells generated and expanded ex vivo with at least one patient specific epitope. In this embodiment, the MHCII restricted CD4$^+$ Foxp3$^+$ regulatory T cells to be used as immunogenic product or in the vaccine composition are generated and expanded ex vivo in the presence of apoptotic bodies of cancer cells obtained from the patient, thereby providing at least one patient specific epitope.

In one embodiment, the immunogenic product, pharmaceutical composition or vaccine composition of the invention comprise, consist essentially of or consist of inactivated MHCII restricted CD4$^+$ Foxp3$^+$ regulatory T cells as active principle.

In one embodiment, the immunogenic product, pharmaceutical composition or vaccine composition of the invention comprises, consists essentially of or consists of at least $10^4$, $10^5$, $10^6$, $10^7$, $10^8$, $10^9$, $10^{10}$ inactivated MHCII restricted CD4$^+$ Foxp3$^+$ regulatory T cells as active principle.

In one embodiment, the immunogenic product, pharmaceutical composition or vaccine composition of the invention comprise, consist essentially of or consist of about $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$, inactivated MHCII restricted CD4$^+$ Foxp3$^+$ regulatory T cells as active principle.

In one embodiment, the MHCII restricted CD4+ Foxp3+ regulatory T cells, the inactivated MHCII restricted CD4+ Foxp3+ regulatory T cells, the immunogenic product, the pharmaceutical composition or the vaccine composition of the invention are/is frozen.

In one embodiment, the immunogenic product, pharmaceutical composition or vaccine composition of the invention may be administrated to the subject by subcutaneous, intramuscular, intraperitoneal or intravenous injection, or directly into the tumor.

In one embodiment, the immunogenic product, pharmaceutical composition or vaccine composition of the invention may be administrated to the subject at least once, twice, 3 times, 4 times, 5 times in a year. Example of regime of administration includes, but is not limited to, administration of the immunogenic product or vaccine composition at day 0, 4 weeks after day 0, 8 weeks after day 0, 12 weeks after day 0 and 24 weeks after day 0.

Another object of the invention is a method for treating cancer in a subject in need thereof, comprising administering to the subject a therapeutically effective amount of inactivated MHCII restricted CD4+ Foxp3+ regulatory T cells or of the immunogenic product, pharmaceutical composition or vaccine composition of the invention as described here above.

Another object of the invention is a method for eliciting an immune response against MHCII restricted CD4+ Foxp3+ regulatory T cells present in the TILs of a subject affected with a cancer, comprising administering to the subject a therapeutically effective amount of inactivated MHCII restricted CD4+ Foxp3+ regulatory T cells or of the immunogenic product, pharmaceutical composition or vaccine composition of the invention as described here above.

Examples of cancer that can be treated with the immunogenic product, pharmaceutical composition or vaccine composition of the invention include, but are not limited to, adrenocortical carcinoma, anal cancer, bladder cancer, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, small cell lymphoma, AIDS-related, lymphoma, central nervous system (primary) lymphoma, cutaneous T-cell lymphoma, Hodgkin's disease, non-Hodgkin's disease, malignant mesothelioma, melanoma, merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, paranasal sinus and nasal cavity cancer, parathyroid cancer, pheochromocytoma cancer, pituitary cancer, plasma cell neoplasm, rhabdomyosarcoma, rectal cancer, renal cell cancer, salivary gland cancer, Sezary syndrome, Kaposi's sarcoma, small intestine cancer, soft tissue sarcoma, thymoma, malignant thyroid cancer, urethral cancer, uterine cancer, sarcoma, unusual cancer of childhood, vaginal cancer, vulvar cancer or Wilms' tumor, benign conditions associated with chemotherapy treatments, such as, lupus, rheumatoid arthritis and skin diseases.

In one embodiment, the cancer that can be treated with the immunogenic product, pharmaceutical composition or vaccine composition of the invention include, but is not limited to, breast cancer, prostate cancer, ovarian cancer and glioblastoma.

Another object of the invention is a method for preparing the immunogenic product of the invention, comprising:
  providing a biological sample, preferably a blood sample, from the subject to be treated and optionally a tumor sample, from the subject to be treated,
  generating and expanding ex vivo as described here above MHCII restricted CD4+ Foxp3+ regulatory T cells from the CD3+ CD4+ CD25− T cells, preferably CD3+ CD4+ CD25− CD45RA+ T cells, isolated from the biological sample,
  inactivating the MHCII restricted CD4+ Foxp3+ regulatory T cells obtained in the previous step,
  thereby obtaining the immunogenic product of the invention.

In a preferred embodiment, the generation and expansion steps are carried out in the presence of tolerogenic dendritic cells (DCs), and pulsed with apoptotic tumor bodies obtained from the tumor sample of the subject.

Another object of the invention is a method for treating cancer in a subject in need thereof, comprising administrating to the subject the immunogenic product, pharmaceutical composition or vaccine composition of the invention.

Another object of the invention is a method for treating cancer in a subject in need thereof, comprising:
  preparing an immunogenic product as described here above,
  optionally preparing a pharmaceutical composition or a vaccine composition comprising the immunogenic product,
  optionally submitting the subject to plasmapheresis,
  administrating to the subject the immunogenic product, pharmaceutical composition or vaccine composition of the invention.

Without wishing to be bound by a theory, the inventors suggest that the MHCII restricted CD4+ Foxp3+ regulatory T cells of the invention, which are committed to exert immune suppressive function, may be capable of inhibiting autoreactive pathogenic immune effector cells including CD4+, CD8+, B cells or innate NK cells, which, in turn, are no longer able to exert their cytotoxic properties towards the self-cells.

One object of the invention is a pharmaceutical composition comprising, consisting essentially of or consisting of the MHCII restricted CD4+ Foxp3+ regulatory T cells or MHCII restricted CD4+ Foxp3+ regulatory T cell population as described here above and at least one pharmaceutically acceptable excipient.

Another object of the invention is a pharmaceutical composition comprising, consisting essentially of or consisting of MHCII restricted CD4+ Foxp3+ regulatory T cells having the following phenotype CD3+ CD4+ Foxp3+ and at least one pharmaceutically acceptable excipient.

Another object of the invention is a pharmaceutical composition comprising, consisting essentially of or consisting of MHCII restricted CD4+ Foxp3+ regulatory T cells having the following phenotype CD3+ CD4+ Foxp3+ generated and expanded ex vivo by the method as described here above and at least one pharmaceutically acceptable excipient.

One object of the invention is the MHCII restricted CD4+ Foxp3+ regulatory T cells or the MHCII restricted CD4+ Foxp3+ regulatory T cell population or the pharmaceutical composition as described here above for use in adoptive therapy.

Another object of the invention is the MHCII restricted CD4+ Foxp3+ regulatory T cells or the MHCII restricted CD4+ Foxp3+ regulatory T cell population or the pharmaceutical composition as described here above for use in treating inflammatory or autoimmune diseases.

Examples of inflammatory or autoimmune diseases include, but are not limited to, acute disseminated encephalomyelitis, acute necrotizing haemorrhagic leukoencephalitis, Addison's disease, agammaglobulinaemia, alopecia areata, amyloidosis, ankylosing spondylitis, anti-GBM/Anti-TBM nephritis, antiphospholipid syndrome, autoimmune angioedema, autoimmune aplastic anaemia, autoimmune dysautonomia, autoimmune haemolytic anaemia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal and neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy, chronic recurrent multifocal osteomyelitis, Churg-Strauss syndrome, cicatricial pemphigoid/benign mucosal pemphigoid, Crohn's disease, Cogans' syndrome, cold agglutinin disease Congenital heart block, Coxsackie myocarditis, CREST disease, essential mixed cryoglobulinemia, demyelinating neuropathies, dermatitis herpetiformis, dermatomyositis, Devic's disease, discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis, giant cell myocarditis, glomerulonephritis, Goodpasture's syndrome, granulomatosis with Polyangiitis (Wegener's syndrome), Graves' disease, Guillain-Barre syndrome, Hashimoto's encephalitis, Hashimoto's thyroiditis, haemo lytic anaemia, Henoch-Schonlein purpura, herpes gestationis, hypogammaglobulinemia, idiopathic pulmonary fibrosis, idiopathic thrombocytopenic purpura, IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease, lupus, Lyme chronic disease, Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism, paediatric autoimmune neuropsychiatric disorders associated with Streptococcus, paraneoplastic cerebellar degeneration, paroxysmal nocturnal hemoglobinuria, Parry Romberg syndrome, Parsonnage-Turner syndrome, pars planitis (peripheral uveitis), pemphigus, peripheral neuropathy, perivenous encephalomyelitis, pernicious anaemia, POEMS syndrome, polyarteritis nodosa, type I, II, and III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, pyoderma gangrenosum, pure red cell aplasia, Raynauds phenomenon, reactive arthritis, reflex sympathetic dystrophy, Reiter's syndrome, Relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, Stiff person syndrome, subacute bacterial endocarditis, Susac's syndrome, sympathetic ophthalmia, systemic lupus erythematosus, Takayasu's arteritis, temporal arteritis/Giant cell arteritis, thrombocytopenic purpura, Tolosa-Hunt syndrome, transverse myelitis, type 1 diabetes, ulcerative colitis, undifferentiated connective tissue disease, uveitis, vasculitis, vesiculobullous dermatosis and vitiligo.

Examples of inflammatory or autoimmune diseases include, but are not limited to, rheumatoid arthritis, type 1 diabetes, and multiple sclerosis.

Another object of the invention is the MHCII restricted CD4+ Foxp3+ regulatory T cells or the MHCII restricted CD4+ Foxp3+ regulatory T cell population or the pharmaceutical composition as described here above for use in preventing transplant rejection, graft versus host disease (GVHD).

In one embodiment, the MHCII restricted CD4+ Foxp3+ regulatory T cells are specific of at least one self-peptide antigen as described here above.

In another embodiment, the MHCII restricted CD4+ Foxp3+ regulatory T cells are specific of at least one self-peptide antigen that were present in tissue lysates.

In one embodiment, the pharmaceutical composition of the invention comprises, consists essentially of or consists of at least $10^4$, $10^5$, $10^6$, $10^7$, $10^8$, $10^9$, $10^{10}$ MHCII restricted CD4+ Foxp3+ regulatory T cells as active principle.

In one embodiment, the pharmaceutical composition of the invention comprises, consists essentially of or consists of about $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$ MHCII restricted CD4+ Foxp3+ regulatory T cells as active principle.

In one embodiment, the MHCII restricted CD4+ Foxp3+ regulatory T cells, the MHCII restricted CD4+ Foxp3+ regulatory T cell population or the pharmaceutical the invention are/is frozen.

In one embodiment, the MHCII restricted CD4+ Foxp3+ regulatory T cells present in the pharmaceutical composition of the invention are human MHCII restricted CD4+ Foxp3+ regulatory T cells.

In one embodiment, the MHCII restricted CD4+ Foxp3+ regulatory T cells present in the pharmaceutical composition of the invention are autologous MHCII restricted CD4+ Foxp3+ regulatory T cells.

In one embodiment, the MHCII restricted CD4+ Foxp3+ regulatory T cells present in the pharmaceutical composition of the invention are allogenic MHCII restricted CD4+ Foxp3+ regulatory T cells.

In one embodiment, the pharmaceutical composition of the invention may be administrated to the subject by subcutaneous, intramuscular, intraperitoneal or intravenous injection.

In one embodiment, the pharmaceutical composition of the invention may be administrated to the subject at least once, twice, 3 times, 4 times, 5 times per week.

In another embodiment, the pharmaceutical composition of the invention may be administrated to the subject at least once, twice, 3 times, 4 times, 5 times per month.

In another embodiment, the pharmaceutical composition of the invention may be administrated to the subject at least once, twice, 3 times, 4 times, 5 times per 3 months.

Another object of the invention is a method for treating inflammatory or autoimmune diseases in a subject in need thereof, comprising administering to the subject a therapeutically effective amount of the MHCII restricted CD4$^+$ Foxp3$^+$ regulatory T cells or the MHCII restricted CD4$^+$ Foxp3$^+$ regulatory T cell population or the pharmaceutical composition as described here above.

It has been shown in the art that T cell vaccination induces regulatory networks that specifically suppress the immunogenic T cells by activating T cells specific for a clonotype-specific determinant (anti-idiotypic response). In addition, anti-ergotypic responses directed at activation markers (corresponding to the ergotope) may also partially account for the suppression of the regulatory T cell population targeted.

Another object of the invention is an antibody recognizing the TCR (T cell receptor) of the MHCII restricted CD4$^+$ Foxp3$^+$ regulatory T cells of the invention.

In one embodiment, the antibody recognizing the TCR of the MHCII restricted CD4$^+$ Foxp3$^+$ regulatory T cells of the invention recognizes at least one of the CDR1, CDR2 and CDR3 (complementary determining region 1, 2 and 3) of the TCR.

In another embodiment, the antibody recognizing the TCR of the MHCII restricted CD4$^+$ Foxp3$^+$ regulatory T cells of the invention recognizes the CDR3 of the TCR.

Another object of the invention is a pharmaceutical composition comprising, consisting essentially of or consisting of said antibody and at least one pharmaceutically acceptable excipient.

Another object of the invention is the use of said antibody for treating cancer in a subject in need thereof.

In one embodiment, the antibodies directed against the MHCII restricted CD4$^+$ Foxp3$^+$ regulatory T cells of the invention consist of antibodies produced following immunization of a mammal, including a human, with the immunogenic composition as described here above.

In another embodiment, the antibodies may also be obtained by cloning the relevant DNA material encoding them, starting for example from B cells obtained from the said mammal, including from the said human.

In another embodiment, the antibodies may also be obtained by sequencing the amino acid sequences of the antibodies collected from the said mammal, including from the said human, and then synthesize a DNA molecule encoding the antibody or a portion thereof comprising the CDR thereof, for producing relevant recombinant antibodies directed against the MHCII restricted CD4$^+$ Foxp3$^+$ regulatory T cells of the invention.

Preparing antibodies directed against the MHCII restricted CD4$^+$ Foxp3$^+$ regulatory T cells of the invention by immunization with the immunogenic composition of the invention may be easily performed by a skilled in the art, using the common technical knowledge from the state in the art.

Alternatively, the antibodies directed against the MHCII restricted CD4$^+$ Foxp3$^+$ regulatory T cells of the invention may be obtained after immortalization of the human B lymphocytes producing them; their cDNA can also be cloned and used further for producing them or their derivatives through recombinant DAN technology.

The term "antibody" herein is used to refer to a molecule having a useful antigen binding specificity. Those skilled in the art will readily appreciate that this term may also cover polypeptides or derivatives of antibodies yet which can show the same or a closely similar functionality. Such antibody fragments or derivatives are intended to be encompassed by the term antibody as used herein. By "antibody" or "antibody molecule" for the purpose of passive immunotherapy, it is intended herein not only whole immunoglobulin molecules but also fragments thereof, such as Fab, F(ab')2, Fv and other fragments thereof that retain the capacity to bind and inactivate the MHCII restricted CD4$^+$ Foxp3$^+$ regulatory T cells. Similarly, the term antibody includes genetically engineered derivatives of antibodies such as single chain Fv molecules (scFv) and domain antibodies (dAbs).

In some embodiments, an antibody directed against the MHCII restricted CD4$^+$ Foxp3$^+$ regulatory T cells of the invention consists of a polyclonal antibody.

In some embodiments, an antibody directed against the MHCII restricted CD4$^+$ Foxp3$^+$ regulatory T cells of the invention consists of a monoclonal antibody.

The term "monoclonal antibody" is used herein to encompass any isolated Ab's such as conventional monoclonal antibody hybridomas, but also to encompass isolated monospecific antibodies produced by any cell, such as for example a sample of identical human immunoglobulins expressed in a mammalian cell line.

The variable heavy (VH) and variable light (VL) domains of the antibody are involved in antigen recognition, a fact first recognized by early protease digestion experiments. Further confirmation was found by "humanization" of rodent antibodies. Variable domains of rodent origin may be fused to constant domains of human origin such that the resultant antibody retains the antigenic specificity of the rodent parented antibody (Morrison et al. (1984) Proc. Natl. Acad. Sci. USA 81, 6851-6855). That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the V.sub.H and V.sub.L partner domains are linked via a flexible oligopeptide (Bird et al (1988) Science 242, 423; Huston et al (1988) Proc. Natl. Acad. Sci. USA 85, 5879) and single domain antibodies (dabs) comprising isolated V domains (Ward et al (1989) Nature 341, 544). A general review of the techniques involved in the synthesis of antibody fragments which retain their specific binding sites is to be found in Winter & Milstein (1991, Nature 349, 293-299).

The term "ScFv molecules" encompasses molecules wherein the VH and VL partner domains are linked via a flexible oligopeptide. Engineered antibodies, such as ScFv antibodies, can be made using the techniques and approaches described in J. Huston et al, (1988) "Protein engineering of antibody binding sites: recovery of specific activity in an anti-digoxin single chain Fv analogue produced in *E. coli*", Proc. Natl. Acad. Sci. USA, 85, pp. 5879-5883, and in A. Pluckthun, (1991) "Antibody engineering; Advances from use of *E. coli* expression systems", Bio/technology 9 (6): 545-51, incorporated herein by reference.

Suitable monoclonal antibodies which are reactive as described herein may be prepared by known techniques, for example those disclosed in "Monoclonal Antibodies; A manual of techniques", H Zola (CRC Press, 1988) and in "Monoclonal Hybridoma Antibodies: Techniques and Application", S G R Hurrell (CRC Press, 1982).

A further embodiment encompasses humanized antibodies where the regions of the murine antibody that contacted the antigen, the Complementarity Determining Regions (CDRs) were transferred to a human antibody framework.

Such antibodies are almost completely human and seldom cause any harmful antibody responses when administered to patients. Several chimeric or humanized antibodies have been registered as therapeutic drugs and are now widely used within various indications (Borrebaeck & Carlsson, 2001, Curr. Opin. Pharmacol. 1: 404-408).

It is preferred if the antibody is a humanized antibody. Suitably prepared non-human antibodies can be "humanized" in known ways, for example by inserting the CDR regions of mouse antibodies into the framework of human antibodies. Humanized antibodies can be made using the techniques and approaches described in Verhoeyen et al (1988) Science, 239, 1534-1536, and in Kettleborough et al, (1991) Protein Engineering, 14 (7), 773-783.

In another embodiment, antibodies also encompass completely human antibodies, which may be produced using recombinant technologies. Typically, large libraries comprising billions of different antibodies are used. In contrast to the previous technologies employing chimerization or humanization of e.g. murine antibodies this technology does not rely on immunization of animals to generate the specific antibody. Instead the recombinant libraries comprise a huge number of pre-made antibody variants wherein it is likely that the library will have at least one antibody specific for any antigen.

The frequency of administration may be determined clinically by following the decline of antibody titers in the serum of patients over time, but in any event may be at a frequency of 1 to 52 times per year, and most preferably between 1 and 12 times per year. Quantities of antibody may vary according to the severity of the disease, or half-life of the antibody in the serum, but preferably will be in the range of 1 to 10 mg/kg of patient, and preferably within the range of 1 to 5 mg/kg of patient, and most preferably 1 to 2 mg/kg of patient.

BRIEF DESCRIPTION OF THE DRAWINGS

FIG. 3: Comparative analysis of in vitro suppressive capacity of human Treg generated with different nTreg polarizing medium. Suppressive capacity of ex vivo generated Treg was evaluated (A) in quiescent and (B) in inflammatory context with the standard polyclonal nTreg assay. CFSE-labeled conventional T cells (Tconv) were cocultured with ex vivo generated Treg at different ratio. Percent inhibition of TconvCFSE proliferation by Treg was depicted. Fresh Treg and Tconv were used as control.

FIG. 7: Suppressive capacity of ex vivo generated OVA-specific Treg after 21 days of culture evaluated with the standard polyclonal nTreg assay. After magnetic depletion of resting CD4$^+$ naive T cells, suppressive capacity of expanded pTreg, was evaluated (A) in quiescent and (B) in inflammatory context. CFSE-labeled Tconv (TconvCFSE) were cocultured with ex vivo generated Tregs at different ratios under the indicated polyclonal stimulations. Proliferation of TconvCFSE was evaluated by the CFSE dilution assay. Fresh Treg were used as control.

FIG. 11: Analysis of IL-1R1 expression in human MHCII restricted CD4$^+$ Foxp3$^+$ CD4$^+$ regulatory T cells (Treg) ex vivo expanded or in vitro induced with different nTreg polarizing medium from conventional or naive CD4$^+$ T cells either after polyclonal or antigen-specific stimulation. Frequency of IL-1R1 expression was evaluated by flow cytometry on the following regulatory T cells population: a) ex vivo resting Tregs isolated from PBMCs, b) ex vivo expanded Tregs from Treg isolated from PBMCs with polyclonal stimulation, c) polyclonal in vitro induced Treg in the presence of Rapa and TGFβ from conventional T cells isolated from PBMCs and d) in vitro induced Ova-specific CD3+ FOXP3$^+$ T cells in presence of Rapa, TGFβ and PGE2 isolated from nave CD4$^+$ T cells. We found that IL-1R1 is preferentially expressed on resting, polyclonal expanded/ induced Tregs when compared to the induced Ova-specific CD3+ FOXP3+ T cells. We also observe that the stability of the suppressive function is inversely correlated with the IL-1R1 expression.

Figure 12:
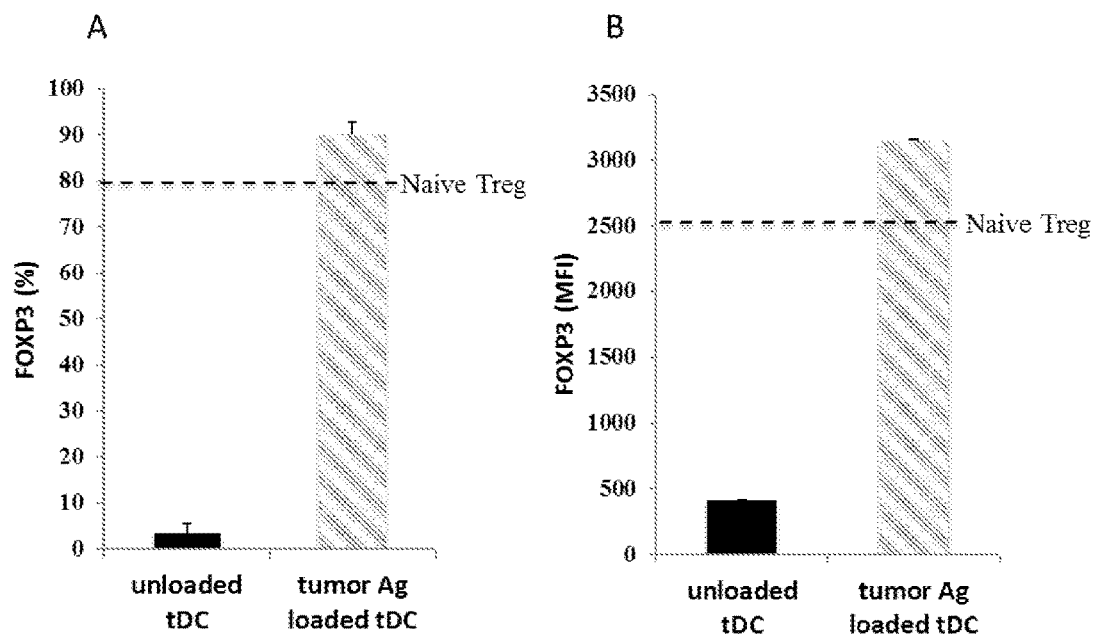

FIG. 12: Analysis of Foxp3+ expression in ex vivo human induced tumor-antigen specific FOXP3 expressing TCRαβ+ MHCII restricted T cells. Apoptotic tumor Ag-pulsed tolerogenic DCs (tDCs) were used to generate and expand specific pTreg from naive CD4+ T cells in the presence of IL-2 (100 IU/ml) and the nTreg polarizing medium composed of TGFβ (5 ng/ml), PGE2 (1 μM) and Rapa (10 nM). Unloaded tDC were used as control. (A) Frequency and (B) expression level (evaluated by MFI) of Foxp3 in CD4+ T cell culture.

Figure 13:
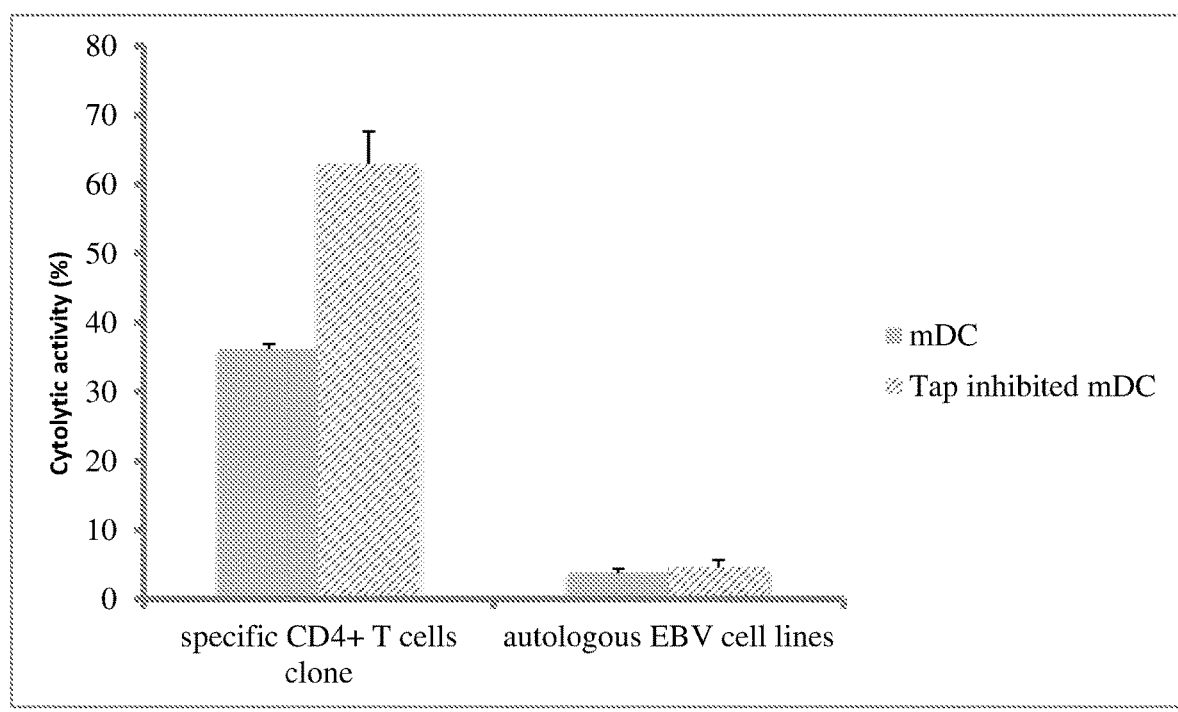

FIG. 13: Generation of autologous CD8+ T cell lines functionally committed to lyse specific pathogenic CD4+ T cells, i.e. tumor-antigen specific FOXP3 expressing TCRαβ+ MHCII restricted T cells. The capacity of a CD8+ T cell clone to lyse its inducing pathogenic CD4+ T cell clone is evaluated with the classical 7-AAD/CFSE Cell-Mediated Cytotoxicity Assay as previously described. In brief, 4 days after stimulation, pathogenic CD4+ target cells or an autologous lymphoblastoid line were labeled with CFSE and placed at $3 \times 10^4$ per well in 96-well U-bottomed plates in triplicate. CD8+ Effector T cells (5:1 E:T ratio) were added, and incubation was carried out at 37° C. for 6 hours. At the end of the experiment, dead cells were labeled with 7-AAD to detect lysed cells. Cytolytic activity against target cells was analyzed based on regions showing double-positive staining CFSE and 7-AAD, using a FACSCalibur instrument. CD8+ T cell clone cytolytic activity (%) was calculated as cells positive for both CFSE and 7-AAD/total CFSE positive cells, after subtracting the spontaneous lysis (%) in negative control. The percentage of cytolytic activity was then calculated using the following equation:

Cytolytic activity (%) [dead target cells (%)–spontaneous death (%)]×100/[100–spontaneous death (%)].

Figure 14:
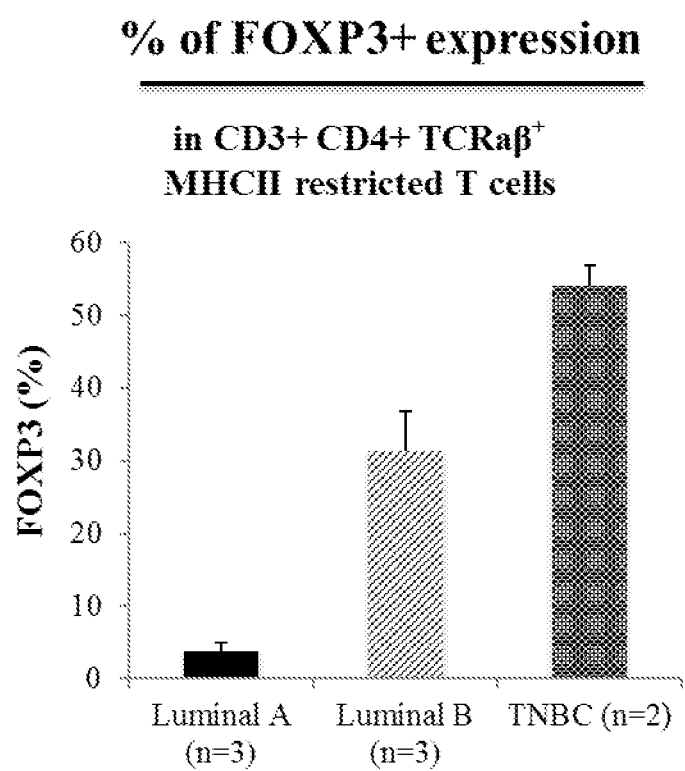

FIG. 14: Analysis of Foxp3+ expression in lymphocytes present in the TILs extracted from 3 different breast cancers' subgroups. Tumor tissue from patient with luminal-A (n=3), luminal B (n=3) and patients with triple-negative breast cancer (TNBC) (n=2) was minced with scalpels and enzymatically digested by overnight incubation in collagenase Type IV. Expression of FOXP3 marker in lymphocytes present in the isolated TIL was determined by flow cytometric analysis. Representation of the percentage of FOXP3 expression in the CD3+ CD4+ TCRαβ+ restricted T cells.

EXAMPLES

The present invention is further illustrated by the following examples.
Materials and Methods
Human Blood Sample. Blood samples from healthy individuals originated from Etablissement Francais du Sang (EFS, Paris). Blood cells are collected using standard procedures.
Human tumor sample. Tumor tissue sample originated from patient with Luminal A and Luminal B Breast cancer (Institut Jean Godinot, Reims).
Cell Purification and Culture.
Peripheral blood mononuclear cells (PBMCs) are isolated by density gradient centrifugation on Ficoll-Hypaque (Pharmacia). PBMCs are used either as fresh cells or stored frozen in liquid nitrogen. T-cell subsets and T cell-depleted accessory cells (ΔCD3 cells) are isolated from either fresh or frozen PBMCs. T cell-depleted accessory cells (ΔCD3 cells) are isolated by negative selection from PBMCs by incubation with anti-CD3-coated Dynabeads (Dynal Biotech) and are irradiated at 3000 rad (referred to as ΔCD3-feeder).

CD3+ T cells are positively selected with a CD3 beads isolation kit (Miltenyi Biotec). Subsequently, selected CD3+ T cells are labeled with anti-CD3 (SK7)-FITC (Becton Dickinson), anti-CD45RA+ (REA562)-FITC (Miltenyi Biotec), and anti-CD27(0323)-APC efluor780 (ebioscience) before being sorted into CD3+ RA+ CD27+ T cells.

CD4+ T cells are negatively selected with a CD4+ T-cell isolation kit (Miltenyi Biotec, yielding CD4+ T-cell populations at a purity of 96-99%. Subsequently, selected CD4+ T cells are labeled with anti-CD4 (13B8.2)-FITC (Beckman Coulter), anti-CD25(4E3)-APC (Miltenyi Biotec), and anti-CD127(R34.34)-PE (Beckman Coulter) before being sorted into CD4+ CD127$^{-/lo}$CD25$^{high}$ (pTregs) and CD4+ CD127+ CD25$^{neg/dim}$ [conventional helper CD4 T cells (Tconv)] subpopulations using a FACSAria III Cell Sorter (Becton Dickinson).

CD14+ monocytes are isolated from PBMCs by positive selection using a MACS system.

CD3+ CD4+ CD127+ CD45RA+ CD25− TCRαβ+ MHCII restricted (naive conventional CD4+ T cells) are isolated from PBMCs after magnetic enrichment (MACS system: CD4 microbeads) and FACs sorting. Before the sorting step, enriched CD3+ CD4+ T cells are stained with anti-CD4 (13B8.2)-FITC (Beckman Coulter), anti-CD25(4E3)-APC (Miltenyi Biotec), and anti-CD127(R34.34)-PE (Beckman Coulter), anti-TCR αβ-BV421 (IP26) (Biolegend).

CD3+ CD45RA+ invTCR Vα24+ CD1-restricted T cells are isolated from PBMCs after magnetic enrichment (MACS system: anti-iNKT microbeads and FACS sorting. Before the sorting step, enriched CD3+ invTCR Vα24+ T cells are stained with anti-CD3 (UCHT-1) V450 anti-invariant TCR Vα24-JαQ (6B11)-PE (inv TCR Vα24-JαQ (Becton Dickinson) and anti-CD45RA (T6D11)-FITC (Miltenyi Biotec).

CD3+ CD45RA+ CD27+ TCRγδ6+ unrestricted T cells are isolated from PBMCs after magnetic enrichment (MACS system: TCRγδ+ T cell isolation kit) and FACS sorting. Before the sorting step, enriched CD3+ TCRγδ+ T cells are stained with anti-CD3 (UCHT-1) V450, anti-TCR panγδ+ PE (IMMU510) (Beckman Coulter), anti-CD27-APC efluor 780 (0323) (ebioscience) and anti-CD45RA (T6D11)-FITC (Miltenyi Biotec).

T cell subsets are cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.

Breast cancer cell line and culture. The human breast cancer cell line MCF-7 was obtained from the American Type Culture Collection (USA). Cells are maintained in Dulbecco's modified Eagle's medium (DMEM; Invitrogen, USA) supplemented with 10% fetal bovine serum (FBS). MCF-7 cells are treated with 5 μg/ml Doxorubicin for 24 h or by γ irradiation (20 Gy). Extent of apoptosis is monitored by flow cytometric analysis (FACS). Cells are extensively washed prior to feeding DCs.

TIL isolation. Tumor tissue was minced with scalpels and enzymatically digested by overnight incubation in collagenase Type IV (2 mg/mL, Roche Diagnostic GmbH) in DMEM High Glucose medium supplemented with 2 mM glutamine (Gibco), 50 mg/mL gentamycin and 0.25% Human Serum Albumin, at 37° C. on a rotary shaker.
Ex Vivo Generation of Polyclonal Functionally Committed FOXP3 Expressing Regulatory T Cells.

Ex vivo generation of polyclonal functionally committed FOXP3 expressing CD3+ TCRαβ+ MHCII restricted T cells: On day 0, T cells are seeded at 2.5×10⁵/well in 48-well plates and stimulated with plate-bound anti-CD3 mAb (4 µg/ml) in the presence of ΔCD3-feeder (1 M). Cells are cultured in IMDM-5 media (IMDM supplemented with 5% SVF, 100 IU/ml penicillin/streptomycin, 1 mM sodium pyruvate, 1 mM nonessential amino acids, glutamax and 10 mM HEPES) with PGE2 1 µM, TGFβ 5 ng/ml, Rapa 10 nM. On day 2, IL-2 (100 IU/ml) are added to the culture. Every three days, half of the supernatant volume is discarded and replaced with fresh IMDM-5 with IL-2 (100 UI/ml). On day 11, these CD4+ T-cell lines were further expanded by restimulation with plate-bound anti-CD3 Abs (4 µg/ml). The restimulations were performed in the presence of ΔCD3-feeder, PGE2 1 µM, TGFβ 5 ng/ml, Rapa 10 nM and IL-2 (100 UI/ml). Then every three days, half of the supernatant volume is discarded and replaced with fresh IMDM-5 with IL-2 (100 UI/ml). On day 20, the phenotype of the expanded CD4+ T cells was assessed by flow cytometry. 75% of the stimulated naive conventional T cells that became CD45RO+ express FOXP3+.

Ex vivo generation of polyclonal functionally committed FOXP3 expressing invariant T cells: On day 0, T cells are seeded at 1×10³/well in 96-well plates and stimulated with plate-bound anti-inv TCR Vα24-JαQ (6B11) mAb (2 µg/ml) in the presence of ΔCD3-feeder (2.5×10⁵). Cells are cultured in IMDM-5 media with PGE2 1 µM, TGFβ5 ng/ml, Rapa 10 nM, IL-2 (100 UI/ml) and IL-15 (10 ng/ml). Every three days, IL-2 (100 UI/ml) and IL-15 (10 ng/ml) are added to the culture. On day 12, T cells are further expanded by restimulation with plate-bound anti-anti-inv TCR Vα24-JαQ (6B11) mAb (2 µg/ml) in the presence of ΔCD3-feeder, PGE2 1 µM, TGFβ 5 ng/ml, Rapa 10 nM IL-2 (100 UI/ml) and IL-15 (10 ng/ml). Then every three days, half of the supernatant volume is discarded and replaced with fresh IMDM-5 with IL-2 (100 UI/ml) and IL-15 (10 ng/ml). On day 21, cells are analyzed by flow cytometry. 70% of the stimulated CD3+ invTCR Vα24+ RA+ T cells that became CD45RO+ express Foxp3+.

Ex vivo generation of polyclonal functionally committed FOXP3 expressing TCRγδ+ T cells: On day 0, T cells are seeded at 1×10³/well in 96-well plates and stimulated with plate-bound anti-TCRγδ mAb (2 µg/ml) in the presence of ΔCD3-feeder (2.5×10⁵). Cells are cultured in IMDM-5 media (IMDM supplemented with 5% SVF, 100 IU/ml penicillin/streptomycin, 1 mM sodium pyruvate, 1 mM nonessential amino acids, glutamax and 10 mM HEPES) with PGE2 1 µM, TGFβ 5 ng/ml, Rapa 10 nM, IL-2 (100 UI/ml) and IL-15 (10 ng/ml). Every three days, half of the supernatant volume is discarded and replaced with fresh IMDM-5 with IL-2 (100 UI/ml) and IL-15 (10 ng/ml). On day 11, T cells were further expanded by restimulation with plate-bound anti-pan TCR γδ Abs (2 µg/ml). The restimulations were performed in the presence of ΔCD3-feeder, PGE2 1 µM, TGFβ 5 ng/ml, Rapa 10 nM and IL-2 (100 UI/ml) and IL-15 (10 ng/ml). Then every three days, half of the supernatant volume is discarded and replaced with fresh IMDM-5 with IL-2 (100 UI/ml) and IL-15 (10 ng/ml). On day 21, cells are analyzed by flow cytometry. 65% of the stimulated CD3+ CD45RA+ CD27+ TCRγδ+ T cells that became CD45RO+ express Foxp3+.

Ex Vivo Generation of Antigen Specific Functionally Committed FOXP3 Expressing T Cells:

Ex vivo generation of antigen (Ovalbumin) specific functionally committed Foxp3 expressing CD3+ TCRαβ+ MHCII restricted T cells:

a) In vitro generation of ovalbumin-loaded Tolerogenic DC from CD14+ monocytes (termed tolerogenic monocyte-derived DC (Tol-Mo-DC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4 for the generation of immature DC. At day 3, 500 µl of the medium containing cytokines was added. On day 6, Tol-Mo-DC are 1) removed from the wells, washed twice with IMDM-5 (IMDM supplemented with 5% SVF, 100 IU/ml penicillin/streptomycin, 1 mM sodium pyruvate, 1 mM nonessential amino acids, glutamax and 10 mM HEPES, 2) added to wells of a 48-well plate at a concentration of 3×10⁵/ml in IMDM-5 and 3) pulsed in IMDM-5 with specific Ag (OVA).

b) Ex vivo generation and expansion of specific functionally committed FOXP3 expressing CD3+ TCRαβ+ MHCII restricted T cells: On day 0, ovalbumin pulsed tDC are 1) washed twice with IMDM-5 and 2) added to wells of a 48-well plate at a concentration of 3×10⁵/ml in IMDM-5 in the presence of 2×10⁵ irradiated autologous feeders, PGE2 1 µM, and Rapa 10 nM. Purified naive conventional CD4+ T cells (isolated from the previously frozen PBMC by FACS) are added to the pulsed tDC. On day 1, IL-2 (100 IU/ml) and TGFβ (5 ng/ml) are added to the coculture. Every three days, half of the supernatant volume is discarded and replaced with fresh IMDM-5 with IL-2 (100 UI/ml (T cell cloning medium). On day 12, these T-cells are further expanded by restimulation with ova-pulsed tDC in the presence of ΔCD3-feeder, PGE2 1 µM, TGFβ 5 ng/ml, Rapa 10 nM, IL-2 (100 UI/ml). Once T cells begin to expand, they can be split every 2 to 3 days with T cell cloning medium and irradiated feeder. On day 21, cells are analyzed by flow cytometry. 85% of the stimulated naive conventional CD4+ T cells that became CD45RO+ express Foxp3+. To confirm that the Ova-specific memory CD3+ TCRαβ+ MHCII restricted T cells are committed to exclusively exert regulatory activity, whatever culture condition of stimulation, after 21 days of expansion in nTreg polarizing medium, the ova-specific-pTreg are further cultured for 3 weeks either in nTreg polarizing medium (comprising the combination of IL-2, TGFβ, PGE2 and rapamycin) or TH-17 polarizing medium (IMDM medium containing IL-2 IL-1 IL-6, IL-21 IL-23 cytokines). The 21-day-expanded-Foxp3 expressing CD3+ CD4+ TCRαβ+ MHCII restricted T cells are stimulated with plate-bound anti-CD3 mAb (4 µg/ml) in the presence of ΔCD3-feeder (1 M) in 48-well plates and every three days, half of the supernatant volume is discarded and replaced with fresh T cell cloning medium or TH-17 polarizing medium for 21 days.

Ex Vivo Generation of Tumor-Antigen Specific Functionally Committed FOXP3 Expressing CD3+ TCRαβ+ MHCII Restricted T Cells:

a) In vitro generation of tumor-loaded tolerogenic DC from CD14+ monocytes (termed tolerogenic monocyte-derived DC (tDC)): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4. At day 3,500 µl of the medium containing cytokines are added. At day 5, a portion of tDCs are co-cultured with apoptotic MCF-7 cells at a DC/tumor cell ratio of 1:2 for 24 h in AIMV with GM-CSF (100 ng/mL), IL-4 (10 ng/mL). Another portion of tDC are frozen at $2 \times 10^6$/per vial in 90% FBS-10% DMSO.

P b) Ex vivo generation and expansion of tumor-antigen specific functionally committed Foxp3 expressing $CD3^+$ $TCR\alpha\beta^+$ MHCII restricted T cells: on day 0, tumor-antigen pulsed tDC are 1) washed twice with IMDM-5 and 2) added to wells of a 48-well plate at a concentration of $3 \times 10^5$/ml in IMDM-5 in the presence of $2 \times 10^5$ irradiated autologous feeders, PGE2 1 µM, and Rapa 10 nM. Purified $CD3^+$ $CD45RA^+$ $TCR\alpha\beta^+$ MHCII restricted T cells (isolated from the previously frozen PBMC by FACS) are added to the pulsed tDC. On day 1, IL-2 (100 IU/ml) and TGFβ (5 ng/ml) are added to the coculture. Every three days, half of the supernatant volume is discarded and replaced with fresh IMDM-5 with IL-2 (100 UI/ml) (T cell cloning medium). On day 12, these T-cells are further expanded by restimulation with tumor Ag-pulsed tDC in the presence of ΔCD3-feeder, PGE2 1 µM, TGFβ 5 ng/ml, Rapa 10 nM and IL-2 (100 UI/ml). Once T cells begin to expand, they can be split every 2 to 3 days with T cell cloning medium and irradiated feeder. On day 21, cells are analyzed by flow cytometry. 88% of the stimulated naive conventional $CD4^+$ T cells that became $CD45RO^+$ express Foxp3$^+$.

Ex Vivo Generation of Tumor-Antigen Specific Functionally Committed FOXP3 Expressing $CD3^+$ invTCR Vα24$^+$ CD1d-Restricted T Cells:

a) In vitro generation of tumor-loaded Tolerogenic DC from $CD14^+$ monocytes (termed tolerogenic monocyte-derived DC (tDC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4 and AM580 (100 nM) for the generation of immature DC expressing CD1d. At day 3, 500 µl of the medium containing cytokines are added. At day 5, a portion of tDCs are co-cultured with apoptotic MCF-7 cells at a DC/tumor cell ratio of 1:2 for 24 h in AIMV with GM-CSF (100 ng/mL), IL-4 (10 ng/mL). Another portion of tDC are frozen at $2 \times 10^6$/per vial in 90% FBS-10% DMSO.

b) Ex vivo generation and expansion of tumor-antigen specific functionally committed Foxp3 expressing $CD3^+$ invTCR Vα24$^+$ CD1d-restricted T cells: On day 0, tumor-antigen pulsed tDC are 1) washed twice with IMDM-5 and 2) added to wells of a 48-well plate at a concentration of $3 \times 10^5$/ml in IMDM-5 in the presence of $2 \times 10^5$ irradiated autologous feeders, PGE2 1 µM, and Rapa 10 nM. Purified $CD3^+$ $CD45RA^+$ invTCR Vα24$^+$ CD1-restricted T cells (isolated from the previously frozen PBMC by FACS) are added to the pulsed tDC. On day 1, IL-2 (100 IU/ml), IL-15 (10 ng/ml) and TGFβ (5 ng/ml) are added to the coculture. Every three days, half of the supernatant volume is discarded and replaced with fresh IMDM-5 with IL-2 (100 UI/ml) and IL-15 (10 ng/ml) (T cell cloning medium). On day 12, these T-cells are further expanded by restimulation with tumor Ag-pulsed tDC in the presence of ΔCD3-feeder, PGE2 1 µM, TGFβ 5 ng/ml, Rapa 10 nM, IL-2 (100 UI/ml) and IL-15 (10 ng/ml). Once T cells begin to expand, they can be split every 2 to 3 days with T cell cloning medium and irradiated feeder. On day 21, cells are analyzed by flow cytometry. 75% of the stimulated $CD3^+$ $CD45RA^+$ invTCR Vα24$^+$ cells that became $CD45RO^+$ express Foxp3$^+$.

Ex Vivo Generation of Specific Phospho-Antigen Functionally Committed FOXP3 Expressing $CD3^+$ TCRγδ$^+$ Unrestricted T Cells:

a) In vitro generation of Tolerogenic DC from $CD14^+$ monocytes (termed tolerogenic monocyte-derived DC (Tol-Mo-DC): monocytes are cultured in 48-well flat-bottom plates containing 0.5 ml of AIMV per well supplemented with 100 ng/ml recombinant human granulocyte macrophage colony-stimulating factor (GM-CSF) and 10 ng/ml human recombinant IL-4 for the generation of immature DC. At day 3, 500 µl of the medium containing cytokines was added. On day 6, generated Tol-Mo-DC are removed from the wells, washed twice with IMDM-5 (IMDM supplemented with 5% SVF, 100 IU/ml penicillin/streptomycin, 1 mM sodium pyruvate, 1 mM nonessential amino acids, glutamax and 10 mM HEPES, frozen or used for the generation and expansion of phospho-antigen specific functionally committed FOXP3 expressing $CD3^+$ TCRγδ$^+$ unrestricted T cells.

b) Ex vivo generation and expansion of phospho-antigen specific functionally committed FOXP3 expressing $CD3^+$ TCRγδ$^+$ unrestricted T cells: on day 0, tDC are added to wells of a 48-well plate at a concentration of $3 \times 10^5$/ml in IMDM-5 in the presence of $2 \times 10^5$ irradiated autologous feeders, PGE2 1 µM, and Rapa 10 nM and zoledronic acid (100 nM). Purified $CD3^+$ $CD45RA^+$ TCRγδ$^+$ unrestricted T cells (isolated from the previously frozen PBMC by FACS) are added to the pulsed tDC. On day 1, IL-2 (100 IU/ml), IL-15 (10 ng/ml) and TGFβ (5 ng/ml) are added to the coculture. Every three days, half of the supernatant volume is discarded and replaced with fresh IMDM-5 with IL-2 (100 UI/ml) and IL-15 (10 ng/ml) (T cell cloning medium). On day 12, these T-cells are further expanded by restimulation with tDC in the presence of ΔCD3-feeder, PGE2 1 µM, TGFβ 5 ng/ml, Rapa 10 nM, IL-2 (100 UI/ml), IL-15 (10 ng/ml) and zoledronic acid (100 nM). Once T cells begin to expand, they can be split every 2 to 3 days with T cell cloning medium and irradiated feeder. On day 21, cells are analyzed by flow cytometry. 75% of the stimulated $CD3^+$ $CD45RA^+$ TCRγδ$^+$ T cells that became $CD45RO^+$ express Foxp3$^+$.

Ex Vivo Generation of Specific Tumor Phospho-Antigen Functionally Committed FOXP3 Expressing $CD3^+$ TCRγδ$^+$ Unrestricted T Cells:

a) In vitro generation of tumor-loaded tolerogenic DC from $CD14^+$ monocytes (termed tolerogenic monocyte-derived DC (tDC): monocytes are cultured in 48-well flat-bottom plates containing 0.5 ml of AIMV per well supplemented with 100 ng/ml recombinant human granulocyte-macrophage colony-stimulating factor (GM-CSF) and 10 ng/ml human recombinant IL-4. At day 3, 500 µl of the medium containing cytokines is added. At day 5, a portion of tDCs are co-cultured with apoptotic MCF-7 cells at a DC/tumor cell ratio of 1:2 for 24 h in AIMV with GM-CSF (100 ng/mL), IL-4 (10 ng/mL). Another portion of tDC are frozen at $2 \times 10^6$/per vial-in 90% FBS-10% DMSO.

b) Ex vivo generation and expansion of tumor-phospho-antigen specific functionally committed Foxp3 expressing $CD3^+$ TCRγδ$^+$ unrestricted T cells: on day 0, tumor-antigen pulsed tDC are 1) washed twice with IMDM-5 and 2) added to wells of a 48-well plate at a concentration of 3×10$^5$/ml in IMDM-5 in the presence of 2×10$^5$ irradiated autologous feeders, PGE2 1 µM, and Rapa 10 nM. Purified CD3$^+$ CD45RA$^+$ TCRγδ$^+$ unrestricted T cells (isolated from the previously frozen PBMC by FACS) are added to the pulsed tDC. On day 1, IL-2 (100 IU/ml) and TGFβ (5 ng/ml) are added to the coculture. Every three days, half of the supernatant volume is discarded and replaced with fresh IMDM-5 with IL-2 (100 UI/ml) (T cell cloning medium). On day 12, these T cells are further expanded by restimulation with tumor Ag-pulsed tDC in the presence of ΔCD3-feeder, PGE2 1 µM, TGFβ 5 ng/ml, Rapa 10 nM and IL-2 (100 UI/ml). Once T cells begin to expand, they can be split every 2 to 3 days with T cell cloning medium and irradiated feeder. On day 21, cells are analyzed by flow cytometry. 75% of the stimulated naive CD3$^+$ CD45RA$^+$ TCRγδ$^+$ T cells that became CD45RO$^+$ express Foxp3$^+$.

Ex Vivo Expansion of Treg from Treg Isolated from PBMCs According to Classical Protocol Described in the Literature:

CD4$^+$ CD127$^{-/lo}$CD25$^{high}$ (Tregs) are stimulated with plate-bound anti-CD3 mAb (4 µg/ml), soluble anti-CD28 Ab (4 µg/ml) in the presence of ΔCD3-feeder (1 M) and IL-2 (100 UI/ml) and Rapamycin (100 nM). Cells are cultured in IMDM-5 media.

Ex Vivo Induction and Generation of Treg from Conventional Helper CD4+ T Cells Isolated from PBMCs According to Classical Protocol Described in the Literature:

CD4$^+$ CD127$^+$ CD25$^{neg/dim}$ [conventional helper CD4 T cells (Tconv)] are stimulated with plate-bound anti-CD3 mAb (4 µg/ml), soluble anti-CD28 Ab (4 µg/ml) in the presence of ΔCD3-feeder (1 M) TGFβ (5 ng/ml) and Rapamycin (100 nM). Cells are cultured in IMDM-5 media. On day 2, IL-2 (100 IU/ml) are added to the culture. Every three days, half of the supernatant volume is discarded and replaced with fresh IMDM-5 with IL-2 (100 UI/ml). On day 11, these CD4$^+$ T-cell lines were further expanded by restimulation with plate-bound anti-CD3 Abs (4 µg/ml) and anti-CD28 Abs. The restimulations were performed in the presence of ΔCD3-feeder, TGFβ 5 ng/ml, Rapa 10 nM and IL-2 (100 UI/ml). Then every three days, half of the supernatant volume is discarded and replaced with fresh IMDM-5 with IL-2 (100 UI/ml).

Improved Ova-Specific Activation and Expansion of CD3+ CD4+ TCR☐β+ MHCII Restricted T Cells Expressing Foxp3:

Ovalbumin pulsed tDC are 1) washed twice with IMDM-5 and 2) added to wells of a 48-well plate at a concentration of 3×10$^5$/ml in IMDM-5 in the presence of 2×10$^5$ irradiated autologous feeders, PGE2 1 µM, and Rapa 10 nM. Purified naive conventional CD4$^+$ T cells (isolated from the previously frozen PBMC by FACS) are added to the pulsed tDC in the presence of soluble anti-CD28 Abs (1 µg/ml—clone CD28.2) and CD40-Abs (1 µg/ml—clone G28.5). After 16 h of stimulation, cells are washed with PBS (0.5% BSA) and stained for 10 min with anti-CD154 (clone 5C8)-PE and anti-CD4(SK3)-PerCP-eFluor 710. The stained cells are incubated with PE-conjugated microbeads (Miltenyi Biotec) and enriched by using MACS columns (Miltenyi Biotec). Isolated CD154+ T cells are then restimulated and expanded under the same optimal conditions as those described above.

In vitro generation of stimulator cells for MLR assay: monocytes are cultured in 48-Well flat-bottom plates containing 0.5 ml of RPMI-5 per well supplemented with 20 ng/ml recombinant human granulocyte-macrophage colony-stimulating factor (GM-CSF) and 20 ng/ml human recombinant IL-4 for the generation of immature DC (iDC). At day 3, 500 µl of the medium containing cytokines are added. At day 5, a portion of iDC are co-cultured with apoptotic MCF-7 cells at a DC/tumor cell ratio of 1:2 for 24 h in RPMI 1640 supplemented with GM-CSF (20 ng/mL), IL-4 (20 ng/mL) and 5% FBS. Another portion of iDC are freezed at 2×10$^6$/per vial—in 90% FBS-10% DMSO. When indicated, pulsed DCs are matured with tumor necrosis factor α (TNF-α; 20 ng/mL final) and PGE2 (1 µM) for 2 days (mDC). In some experiments, TNF and PGE2 (at the same concentrations), or lipopolysaccharide (LPS; 10-1000 ng/mL; Sigma) are added directly to MLRs. Antigen-loaded DC stimulators are irradiated at 30 Gy.

In vitro generation of TAP-inhibited stimulator cells for MLR assay: matured DC, obtained as described above, are electroporated with 20 µg of RNA synthesized from the pGem4Z vector containing the UL49.5 gene from BHV-1. (ref: Lampen M H, Verweij M C, Querido B, van der Burg S H, Wiertz E J, van Hall T. CD8+T cell responses against TAP-inhibited cells are readily detected in the human population. J Immunol. 2010 Dec. 1; 185(11):6508-17.)

Apoptotic T Cells-DC Cocultures.

Immature DCs were cultured alone or with apoptotic cells (3 apoptotic cells: 1 iDC) for 16 h. DCs were then purified by immunomagnetic depletion of apoptotic T cells using anti-CD3-coated microbeads (Miltenyi Biotec), electroporated or not with 20 µg of synthesized RNA and incubated in RPMI-5 supplemented with 20 ng/ml GM-CSF, 20 ng/ml human recombinant IL-4 and the maturation cocktail (TNF-α 20 ng/ml and PGE2 1 µM) for 24 hours.

IL-17 Detection by ELISA.

The presence of IL-17 in the culture supernatant is measured by ELISA. The recognition of IL-17 by an anti-IL-17 antibody may be carried out by conventional methods known in the art such as a sandwich ELISA anti-IL-17. The ELISA is developed by any colorimetric means known in the art such as for example using detection antibody labelled with biotin, a poly-streptavidin HRP amplification system and an o-phenylenediamine dihydrochloride substrate solution.

One example of said method is the following:
coating a plate with the capture antibody, such as for example an anti-IL17 antibody,
blocking the plate with a blocking buffer (such as casein 2% in PBS for example) during 90 min at 37° C.,
incubating the plate during 90 min at 37° C. with a dilution series of IL-17 standard, samples or negative controls,
incubating the plate 90 min at 37° C. with the detection antibody such as for example a biotinylated anti-IL-17 antibody,
incubating the plate with streptavidin-HRP during 30 min at 37° C. and developing the complex with an o-phenylenediamine dihydrochloride (OPD) substrate solution during 30 min. After stopping the enzymatic reaction, the intensity of the resulting color is determined by spectrophotometric methods at 490 nm.

The person skilled in the art considers that an IL-17 level inferior to 200 ng/ml, 100 ng/ml, 50 ng/ml corresponds to no secretion or low secretion of IL-17 after calculation with the standard curve.

Flow Cytometry Analysis.

mAb labeling. The following conjugated mAbs are used.
a) for CD3$^+$ T cells: anti-CD4(SK3)-PerCP-eFluor 710, anti-TCRαβ (IP26)-APC (ebioscience), anti-CD25 (B1.49.9)-PeCy55, anti-CD127(R34.34)-APC-AF700 (Beckman Coulter), anti-CD3(UCHT1)-BB515 anti-invariant TCR Vα24-JαQ (6B11)-PE, anti-Foxp3 (259D/C7)-PE-CF594 and anti-CD152 (BNI3)-BV421, anti-CD161 (DX12) BV605 and anti-CD56(NCAM 16.2) BU395 (Becton Dickinson), anti-TCR αβ-BV421 (IP26) (Biolegend), anti-TCR pan γδ+ PE (IMMU510) (Beckman Coulter) and anti-CD27− APC efluor 780 (0323) (ebioscience). Cells are stained for surface markers (at 4° C. in the dark for 30 min) using mixtures of Ab diluted in PBS containing BSA/NaN$_3$ (0.5% BSA, 0.01% NaN$_3$) (FACS buffer). Foxp3 and CTLA-4 intracellular staining are performed with FOXP3 staining kit obtained from ebio science according to the manufacturer's instructions. Appropriate isotype control Abs are used for each staining combination. Samples are acquired on a BD LSR FORTESSA flow cytometer using BD FACSDIVA 8.0.1 software (Becton Dickinson). Results are expressed in percentage (%) or in mean fluorescence intensity (MFI).

b) for the induced specific Treg: presence of IL-1R1 on induced Treg was evaluated with the monoclonal anti-Foxp3 (259D/C7)-PE-CF594 Ab and the polyclonal anti-IL-1R1-PE (R&D system, FAB269P).

CFSE staining. Tconv are stained with 1 µM carboxyfluorescein succinimidyl ester (CFSE) (CellTrace cell proliferation kit; Molecular Probes/Invitrogen) in PBS for 8 min at 37° C. at a concentration of $1 \times 10^7$ cells/mL The labeling are stopped by washing the cell twice with RPMI 1640 culture medium containing 10% FBS. Cells are then resuspended at the desired concentration and subsequently used for proliferation assays.

7-AAD (7-amino-actinomycin D) staining. Apoptosis of stimulated CFSE-labeled or unlabeled nTregs and Tconv was determined using the 7-AAD assay. Briefly, cultured cells are stained with 20 µg/mL nuclear dye 7-AAD (Sigma-Aldrich) for 30 min at 4° C. FSC/7-AAD dot plots distinguish living ($FSC^{high}$/7-AAD$^-$) from apoptotic ($FSC^{high}$/7-AAD$^+$) cells and apoptotic bodies ($FSC^{low}$/7-AAD$^+$) and debris (($FSC^{low}$/7-AAD$^-$). Living cells are identified as CD3$^+$7-AAD$^-$ FSC$^+$ cells.

Functional Assays.

T-cell proliferation. T-cell proliferation is assessed CFSE dilution assay in RPMI supplemented with 5% FBS, 100 IU/ml penicillin/streptomycin, 1 mM sodium pyruvate, 1 mM nonessential amino acids, glutamax and 10 mM HEPES (RPMI-5 media) in normoxia. At coculture completion, stimulated CFSE-labeled Tconv are harvested, costained with anti-CD3 mAb and 7-AAD, and the percentage of living proliferating cells (defined as CFSE low fraction) in gated CD3$^+$ 7-AAD$^-$ cells is determined by flow cytometry.

T cell apoptosis induction: tumor-antigen specific functionally committed FOXP3 expressing TCRαβ$^+$ MHCII restricted T cells are generated ex vivo as described above. Then tumor-antigen specific stimulated-T cells were irradiated (240 mJ/cm2) at 254 nm (UV-C) and cultured for 6 hours before coculture with immature DCs. Apoptosis was confirmed by 7-AAD staining. On average, 75% of cells are 7-AAD+.

Standard polyclonal cell-cell contact Treg suppression assay: CFSE-labeled Tconv ($4 \times 10^4$ per well), used as responder cells, are cultured with ΔCD3− feeder ($4 \times 10^4$ per well) in the presence or absence of defined amounts of Foxp3 T cells (blood Treg or ex vivo generated T cells) for 4 to 5 d. Cultures are performed in round-bottom plates coated with 0.2 µg/mL anti-CD3 mAb in 200 µL of complete RPMI medium. Results are expressed as the percentage of proliferating CFSE low T cells or as a percentage of suppression calculated as follows: (100×[(percentage of Tconv CFSE low cells−percentage of Tconv CFSE low in coculture with nTregs)/percentage of Tconv CSFE low cells.

Autologous MLR suppression assay: CFSE-labeled Tconv CD4$^+$ CD25$^-$ T cells ($5 \times 10^4$) are stimulated either with $1 \times 10^4$ pulsed iDC in RPMI-5 media or with $5 \times 10^3$ pulsed mDC in IMDM-5 media supplemented with IL-2 (20 IU/ml) IL-1b (10 ng/ml), IL-6 (30 ng/ml), IL-21 (50 ng/ml) and IL-23 (30 ng/ml) in the presence or absence of defined amounts of Foxp3 T cells (blood Treg or ex vivo generated T cells) for 5 to 6 d. When indicated, culture are performed in IMDM-5 media supplemented with IL-2 (20 IU/ml) IL-1β (10 ng/ml), IL-6 (30 ng/ml), IL-21 (50 ng/ml) and IL-23 (30 ng/ml). Results are expressed as the percentage of proliferating CFSE low T cells or as a percentage of suppression calculated as follows: (100×[(percentage of Tconv CFSE low cells−percentage of Tconv CFSE low in coculture with nTregs)/percentage of Tconv CSFE low cells.

Measurement of DNA methylation: Classically, a stable Treg genetic signature consisted of highly demethylated CpG islands within the conserved non-coding sequence 2 (CNS2) of the Treg specific demethylation region (TSDR). DNA methylation analysis of the TSDR region of the gene FOXP3 was evaluated by quantitative PCR after bisulfite treatment of genomic DNA as previously described by Christopher Fuhrman (Fuhrman et al, Divergent Phenotypes of Human Regulatory T Cells Expressing the Receptors TIGIT and CD226, 2015, Journal of immunology). Briefly Nucleotides were isolated with AllPrep DNA/RNA Mini Kit (Qiagen) or DNeasy tissue kit (Qiagen), as appropriate. Bisulfite treatment of genomic DNA was performed on 500 ng DNA with the EZ DNA Methylation Kit (Zymo Research). DNA standards originated from unmethylated bisulfite-converted human EpiTect control DNA (Qiagen) or universally methylated bisulfite-converted human control DNA (Zymo Research). To obtain a large quantity of standard, the TSDR was PCR-amplified using the following reaction: 50 µl reaction volume containing 25 µl of ZymoTaq PreMix buffer (Zymo Research) and 0.5 µM each of the primers FOXP3_TSDRfwd (5'-ATATTTTAGATAGGGA-TATGGAGATGATTTGTTTGG-3' SEQ ID NO: 1) and FOXP3_TSDRrev (5'-AATAAACATCACCTACCACATC-CACCAACAC-3'-SEQ ID NO: 2). After incubation at 95° C. for 10 min, amplification was performed as follows: 50 cycles at 95° C. for 30 s, 55° C. for 30 s, and 72° C. for 1 min. Amplified PCR products were purified with the QIAquick Gel Extraction Kit (Qiagen). The concentration of purified control TSDR DNA was determined with a GE NanoVue spectrophotometer (GE Healthcare Life Sciences). TSDR real-time PCR was performed with probes that targeted methylated or demethylated target sequences. The reaction was performed in 96-well white trays with a Roche LightCycler 480 system (Roche Diagnostics). Each reaction contained 10 µl LightCycler 480 Probes Master Mix (Roche), 10 ng of bisulfite converted DNA sample or standards, 1 µM of each primer, and 150 nM of each probe with a final reaction value of 20 µl. The probes used for amplification were TSDR-Forward 5'-GGTTTGTAT-TTGGGTTTTGTTGTTATAGT-3' (SEQ ID NO: 3) and TSDR-Reverse 5'-CTATAAAATAAAATATCTACCCTCT-TCTCTTCCT-3' (SEQ ID NO: 4). The probes for target sequence detection were FAM-labeled methylated probe, FAM-CGGTCGGATGCGTC-MGB-NFQ (SEQ ID NO: 5), or VIC-labeled unmethylated probe, VIC-TGGTGGTTG-GATGTGTTG-MGB-NFQ (SEQ ID NO: 6). All samples were tested in triplicate. The protocol for real-time amplification is as follows: after initial denaturation at 95° C. for 10 min, the samples were subjected to 50 cycles at 95° C. for 15 s and at 61° C. for 1 min. Fourteen different ratios of fully methylated and demethylated template were used as real-time standards. A six-order polynomial equation was used to extrapolate the percentage of cells demethylated at the TSDR for each sample.

Measurement of histone acetylation: Histone acetylation analysis of the four different sites of FOXP3 gene was evaluated by ChIP assay, as previously described by Ling Lu (Ling Lu et al, PNAS 2014). Briefly, 50,000 cells of each treated nTreg cell sample were harvested and cross-linked with 1% formaldehyde, and then lysed with 120 µL, of lysis buffer [50 mM Tris.HCl, pH 8.0, 10 mM EDTA, 1% (wt/vol) SDS, protease inhibitor mix (1:100 dilution; Sigma), 1 mM PMSF, 20 mM Na-butyrate]. The chromatin in the lysate was sonicated to 500-800-bp fragments and then diluted with 8004, of RIPA ChIP buffer [10 mM Tris.HCl, pH 7.5, 140 mM NaCl, 1 mM EDTA, 0.5 mM EGTA, 1% (vol/vol) Triton X-100, 0.1% (wt/vol) SDS, 0.1% (wt/vol) Na-deoxycholate, protease inhibitor mix (1:100 dilution; Sigma), 1 mM PMSF, and 20 mM Na-butyrate]. Dynabeads protein G (10 µL; Invitrogen) was incubated with 1 µg of H3K4me3 (Abcam) or H3K9ac (Cell Signaling) or normal rabbit IgG negative control ChIP-grade antibodies for 2 h separately. Then, 100 µL of the sheared chromatin was immunoprecipitated with pretreated antibody-bead complexes and another 100 µL of the sheared chromatin for total input DNA extraction separately. Immunoprecipitated DNA was quantified by real-time PCR with following primers: promoter, 5'-ACC GTA CAG CGT GGT TTT TC-3' (SEQ ID NO: 7) and 5'-CTA CCT CCC TGC CAT CTC CT-3' (SEQ ID NO: 8); CNS1, 5'-CCC AAG CCC TAT GTG TGATT-3' (SEQ ID NO: 9) and 5'-GTG TGT CAG GCC TTG TGC TA-3' (SEQ ID NO: 10); CNS2, 5'-GTC CTC TCC ACAACC CAA GA-3' (SEQ ID NO: 11) and 5'-GAC ACC ACG GAG GAA GAG AA-3' (SEQ ID NO: 12); and CNS3, 5'-AGG TGC CGA CCT TTA CTG TG-3' (SEQ ID NO: 13) and 5'-ACA ATA CGG CCT CCT CCT CT-3' (SEQ ID NO: 14).

Classical 7-AAD/CFSE Cell-Mediated Cytotoxicity Assay: target cells were labeled with CFSE as described above and placed at 3×104 per well in 96-well U-bottomed plates in triplicate. CD8+ Effector T cells (5:1 E:T ratio) were added, and incubation was carried out at 37° C. for 6 hr. At the end of the experiment, dead cells were labeled with 7-AAD to detect lysed cells. Cytolytic activity against target cells was analyzed based on regions showing double-positive staining CFSE and 7-AAD, using a FACSCalibur instrument. CD8+ T cell clone cytolytic activity (%) was calculated as cells positive for both CFSE and 7-AAD/total CFSE positive cells, after subtracting the spontaneous lysis (%) in negative control. The percentage of cytolytic activity was then calculated using the following equation:

Cytolytic activity (%) [dead target cells (%)−spontaneous death (%)]×100/[100−spontaneous death (%)]

Results a) Optimal Conditions for Inducing Foxp3 Expression in Naive CD3$^+$ CD4$^+$ TCRαβ$^+$ MHCII Restricted T Following Polyclonal.

Starting from naive conventional CD4$^+$ T cells (CD3$^+$ CD4$^+$ CD127$^+$ CD45RA$^+$ CD25$^-$ TCRαβ$^+$ MHCII restricted) isolated from human PBMCs, different nTreg polarizing medium were assessed for their capacity to induce the differentiation of Foxp3$^+$ cells with suppressive function.

Figure 1:
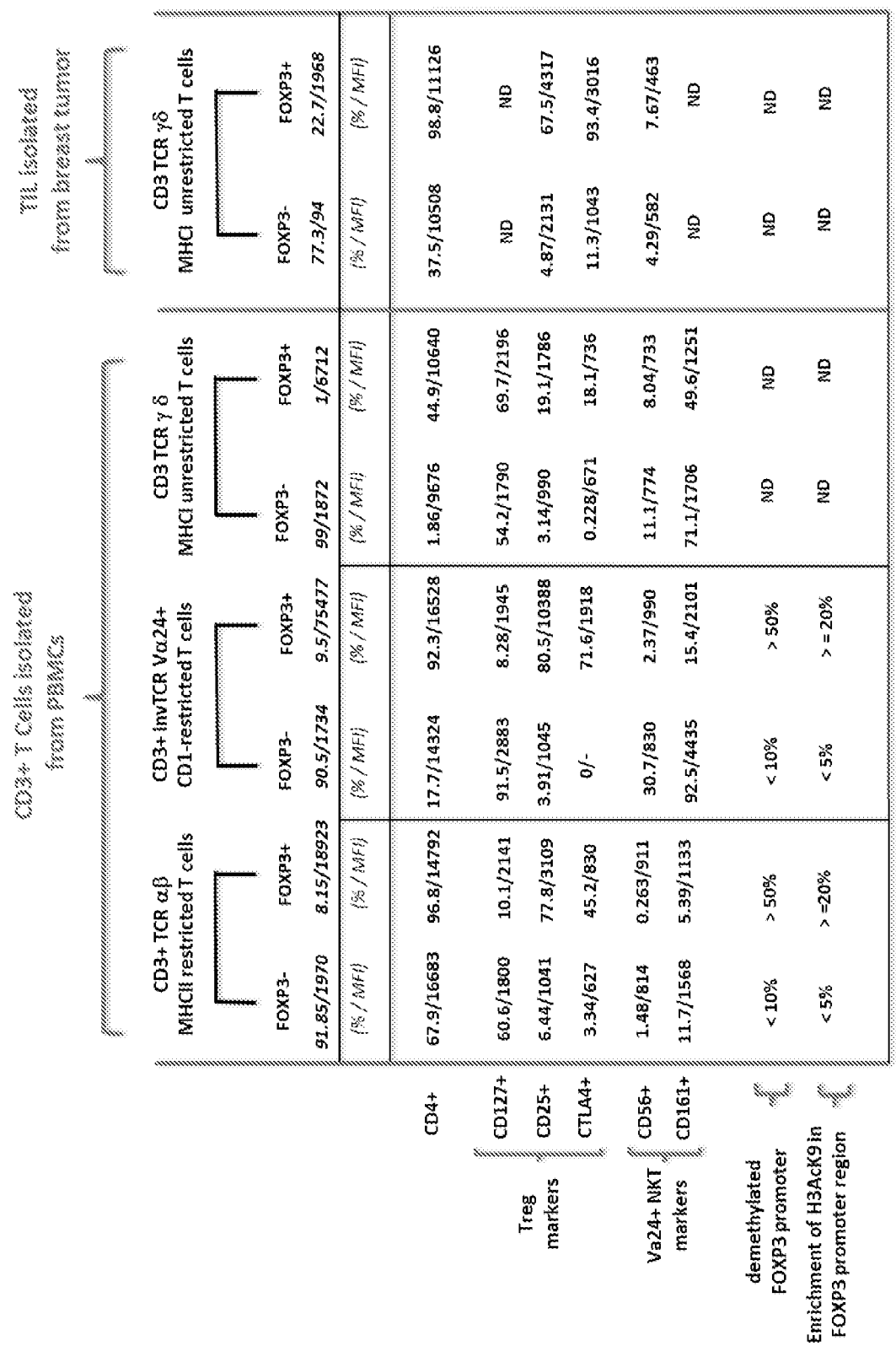
FIG. 1: Different frequencies and phenotypic characteristics between FOXP3$^+$ and FOXP3$^-$ CD3$^+$ T cell populations, as defined by their variable TCR recognition in human peripheral blood (PBMCs) and in TIL isolated from breast tumor.
Figure 2:
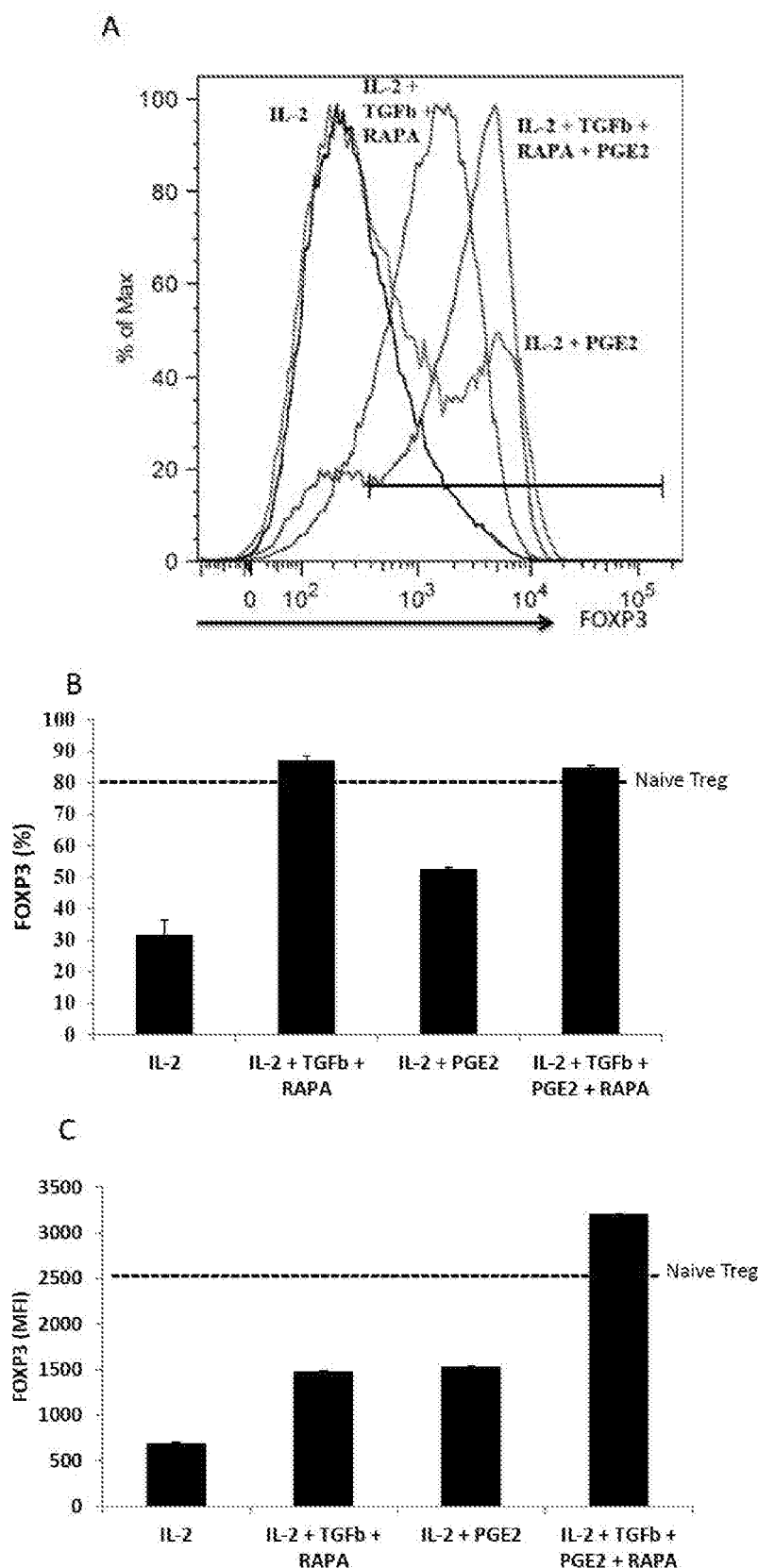
FIG. 2: Analysis of Foxp3$^+$ expression in human MHCII restricted CD4$^+$ Foxp3$^+$ CD4$^+$ regulatory T cells (Treg) generated ex vivo from polyclonally stimulated naive CD4$^+$ T cells with different nTreg polarizing medium. Naive CD4$^+$ T cells were stimulated for 12 days with plate-bound anti-CD3 (4 µg/ml) in presence of IL-2 (100 IU/ml). Where indicated, TGFβ (5 ng/ml), RAPA (10 nM) and PGE2 (1 µM) were added. (A) Overlay histogram displaying Foxp3 expression profiles of each of the generated pTreg. (B) Frequency and (C) expression level (evaluated by MFI) of Foxp3 in CD4$^+$ T cell culture.

FIG. 2 shows that, when ex vivo activated polyclonally with anti-CD3 mAbs, naive conventional CD4$^+$ T cells exhibit a variable level of Foxp3 dependent on their culture condition of stimulation. Polarizing medium comprising the combination of IL-2, TGFβ and rapamycin or IL-2, TGFβ, rapamycin and PGE2 results in a higher Foxp3 expression over combinations of IL-2 and PGE2, or IL-2 alone (B). Moreover, the combination of IL-2, TGFβ, rapamycin and PGE2 results in an optimal intensity of Foxp3 expression in the CD3$^+$ CD4$^+$ TCRαβ$^+$ MHCII restricted T cells, as compared to the other combinations (C).

It is interesting to note that only naive conventional CD4$^+$ T cells, stimulated with the polarizing medium comprising the combination of IL-2, TGFβ, PGE2 and rapamycin, express level and intensity of Foxp3 similar or higher to those of blood nave regulatory T cells (CD3$^+$ TCRαβ$^+$ CD4$^+$ CD127$^{-/low}$ CD45RA$^+$ CD25$^+$), corresponding to our positive control.

We next evaluated the functional suppressive capacity of the Foxp3 expressing CD3$^+$ CD4$^+$ TCRαβ+ MHCII restricted T cells polyclonally stimulated. FIG. 3A shows that CD3$^+$ CD4$^+$ TCRαβ$^+$ MHCII restricted T cells, ex vivo generated and expanded for 21 days, using polyclonal stimulation, in the presence of the nTreg polarizing medium comprising the combination of IL-2, TGFβ, PGE2 and rapamycin, display a higher suppressive activity compared with both those generated in the presence of the nTreg polarizing medium comprising the combination of IL-2, TGFβ, rapamycin without PGE2 and fresh FOXP3 expressing CD3$^+$ CD4$^+$ TCRαβ$^+$ MHCII restricted T cells, when using the standard polyclonal cell-cell contact Treg suppression assay. Furthermore, FIG. 3B shows that these 21-day-expanded-FOXP3 expressing CD3$^+$ CD4$^+$ TCRαβ$^+$ MHCII restricted T cells still maintain their suppressive activity, when the functional suppressive assay is performed in presence of a highly-inflammatory medium containing IL-2 IL-1 IL-6, IL-21 IL-23 cytokines, while fresh FOXP3 expressing CD3$^+$ CD4$^+$ TCRαβ$^+$ MHCII restricted T cells lose their suppressive capacity under these culture condition of stimulation.

b) Optimal Conditions for Inducing Foxp3 Expression in Naive CD3$^+$ CD4$^+$ TCRαβ$^+$ MHCII Restricted T Cells Following Antigen-Specific Activation.

As studies suggested that the suppressive potential of antigen-specific Treg was much greater than that of polyclonal Treg, we set up a method to ex vivo generated and expanded antigen specific Foxp3 expressing CD3$^+$ CD4$^+$ TCRαβ$^+$ MHCII restricted T cells, committed to exclusively exert regulatory activity, whichever culture condition of stimulation.

Figure 4:
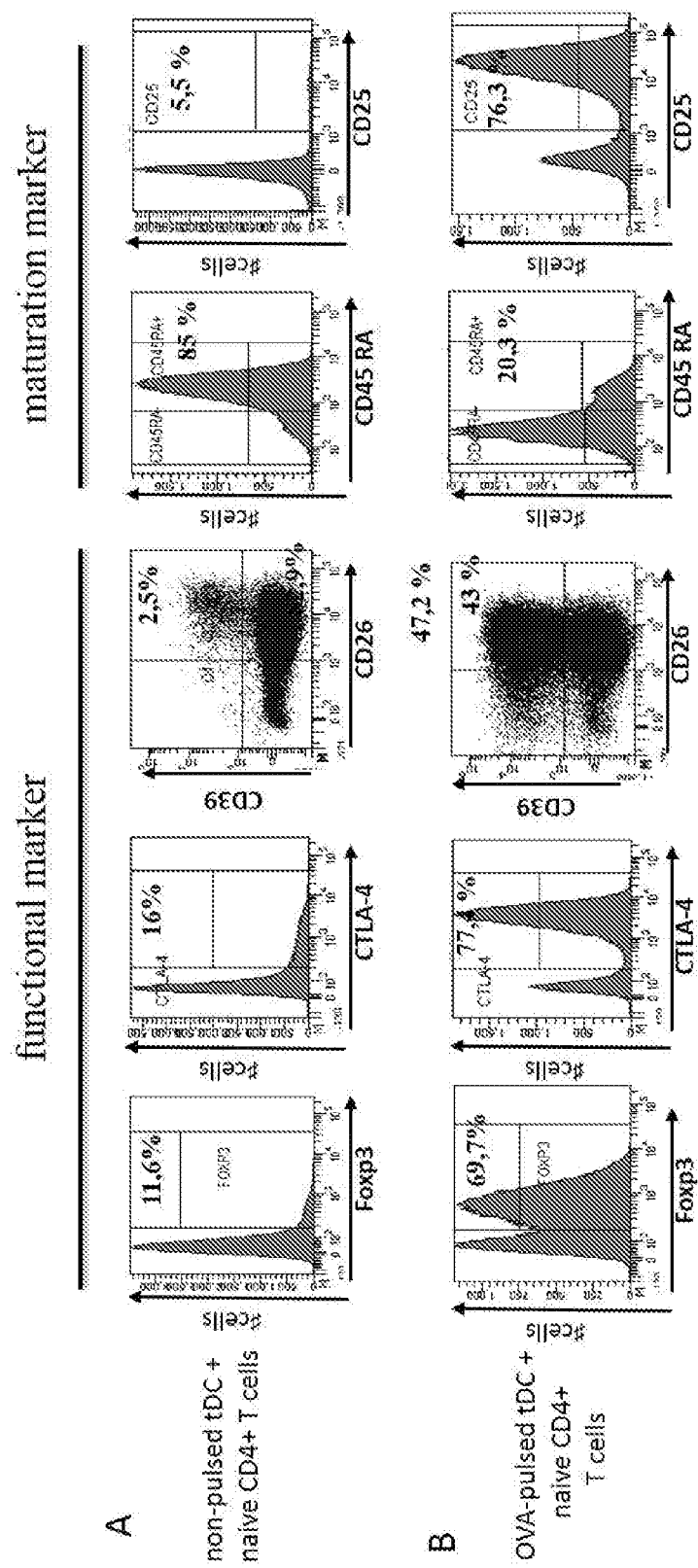
FIG. 4: Phenotype of ex vivo generated Ag-specific Treg after 21 days of culture. Naive CD4$^+$ T cell were stimulated with (A) non-pulsed autologous tDCs or (B) with OVA-pulsed autologous tDCs, in presence of IL-2 and defined nTreg polarizing medium. Stimulated CD4$^+$ T cells were stained at the cell surface using Abs directed against CD45RA, CD25, CD26, CD39. After fixation and permeabilization Foxp3 and CTLA4 were stained intracellularly.
Figure 5:
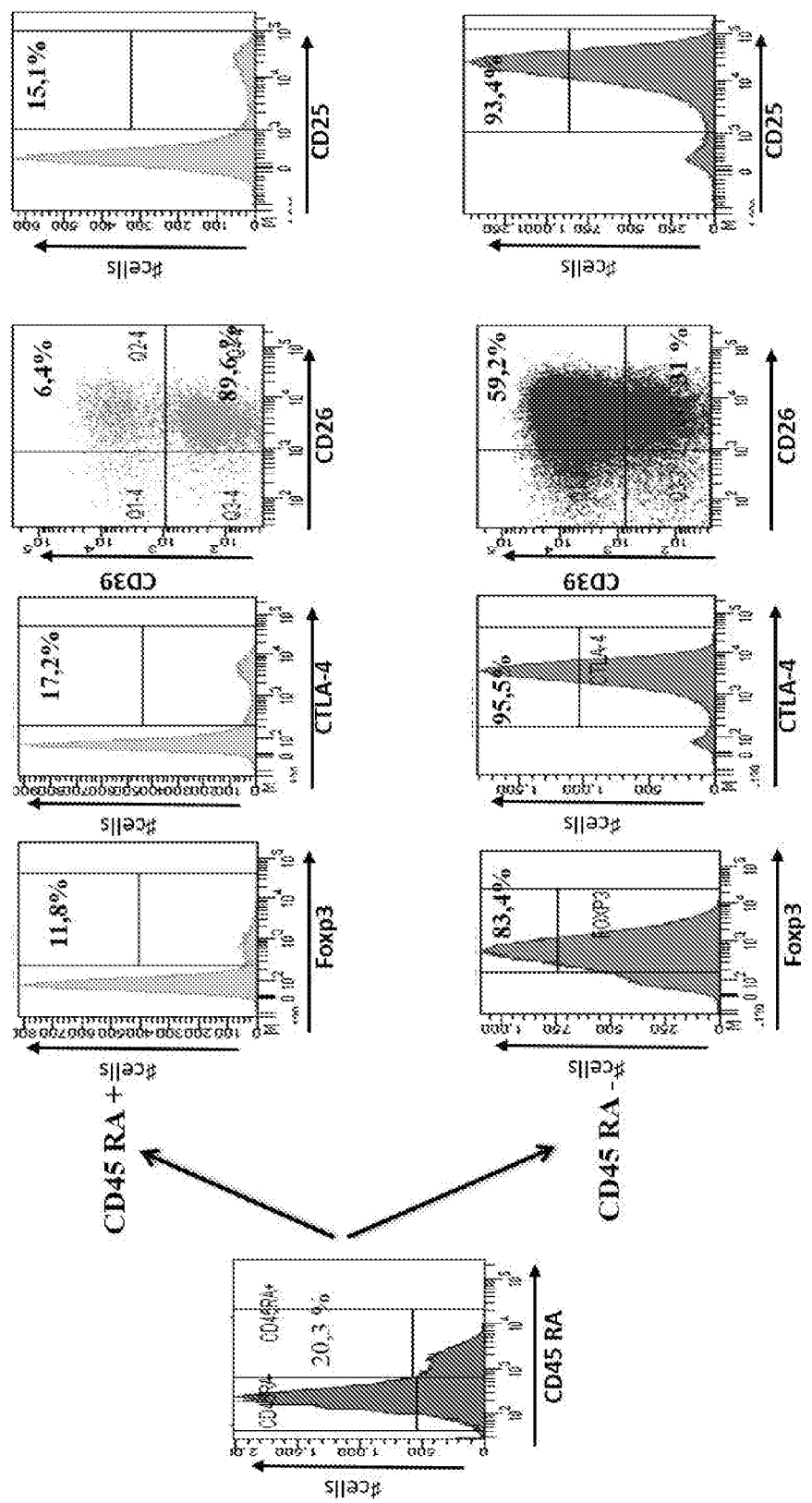
FIG. 5: Contamination of ex vivo generated OVA-specific Treg with unstimulated naive CD4+ T cells. Cells were stained with CD45RA, Foxp3, CTL14, CD26 and CD25.

FIG. 4 shows that OVA-pulsed autologous tDCs, in presence of the nTreg polarizing medium comprising the combination of IL-2, TGFβ, PGE2 and rapamycin are able to stimulate naive conventional CD4+ T cells, (increase expression of CD25 and loss of CD45RA marker), while non-pulsed autologous tDCs, in presence of the same polarizing medium, were unable to stimulate them (absence of CD25 expression and persistence of CD45RA marker). Furthermore, naive conventional CD4$^+$ T cells, when specifically activated and expanded for 21 days with OVA-pulsed autologous tDCs, in presence of the nTreg polarizing medium described above, are able to express similar level and intensity of Foxp3 to those displayed by blood nave regulatory T cells (CD3$^+$ TCRαβ$^+$ CD4$^+$ CD127$^{-/low}$ CD45RA$^+$ CD25$^+$), corresponding to our positive control (FIG. 5).

Figure 6:
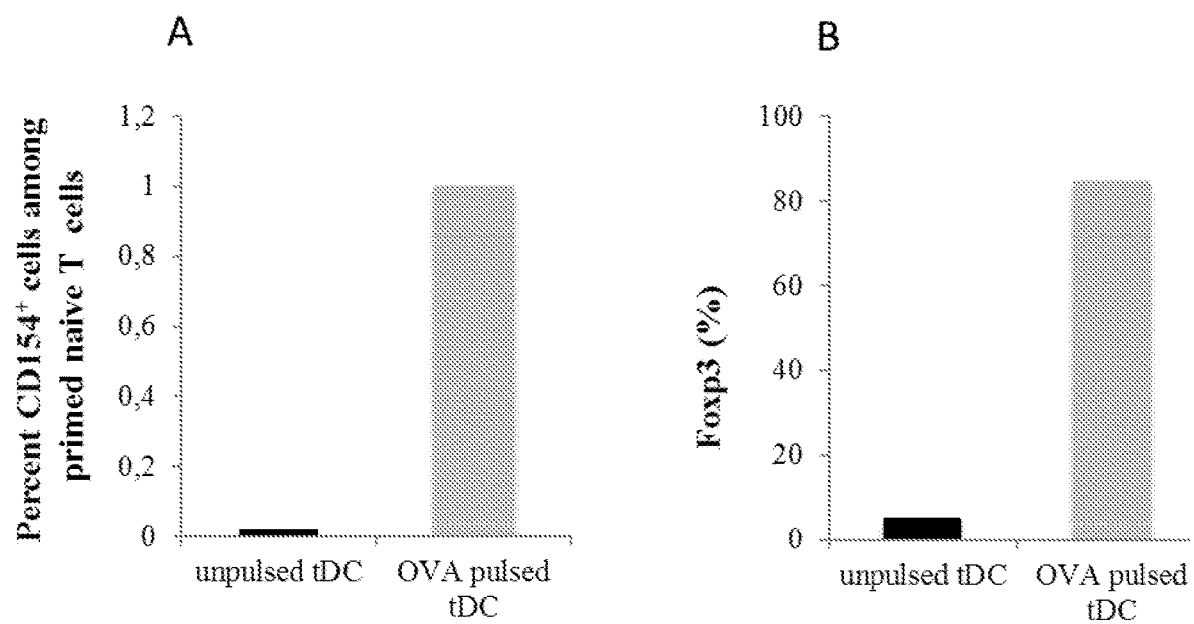
FIG. 6: CD154 expression analysis on nave CD3$^+$ CD4$^+$ TCRαβ$^+$ T cells primed with Ova pulsed tDC and Foxp3 expression in expanded Ova specific generated Treg. A-Frequency of CD154$^+$ expression among primed nave CD3$^+$ CD4$^+$ TCRαβ$^+$ T cells, 16 h after their stimulation with either unpulsed tDC or Ova pulsed as described in Material and Methods. B-Foxp3 expression in ex vivo generated Ag-specific Treg after 21 days of culture in nTreg polarizing medium.

To improve the antigen specific activation and expansion of nave CD3$^+$ CD4$^+$ TCRαβ+ MHCII restricted T cells expressing Foxp3, 16 h after their priming with OVA-pulsed autologous tDCs in the presence of soluble anti-CD28 Abs (1 m/ml) and CD40-Abs (1 µg/ml), CD154 expressing nave CD3+ CD4+ TCRαβ+ T cells are sorted (FIG. 6). Isolated CD154+ T cells are then restimulated and expanded under the same optimal conditions as those described above. Using this strategy, we are able to ex vivo induce and generate highly specific functionally committed FOXP3 expressing CD3+ TCRαβ+ MHCII restricted T cells lines.

Figure 8:
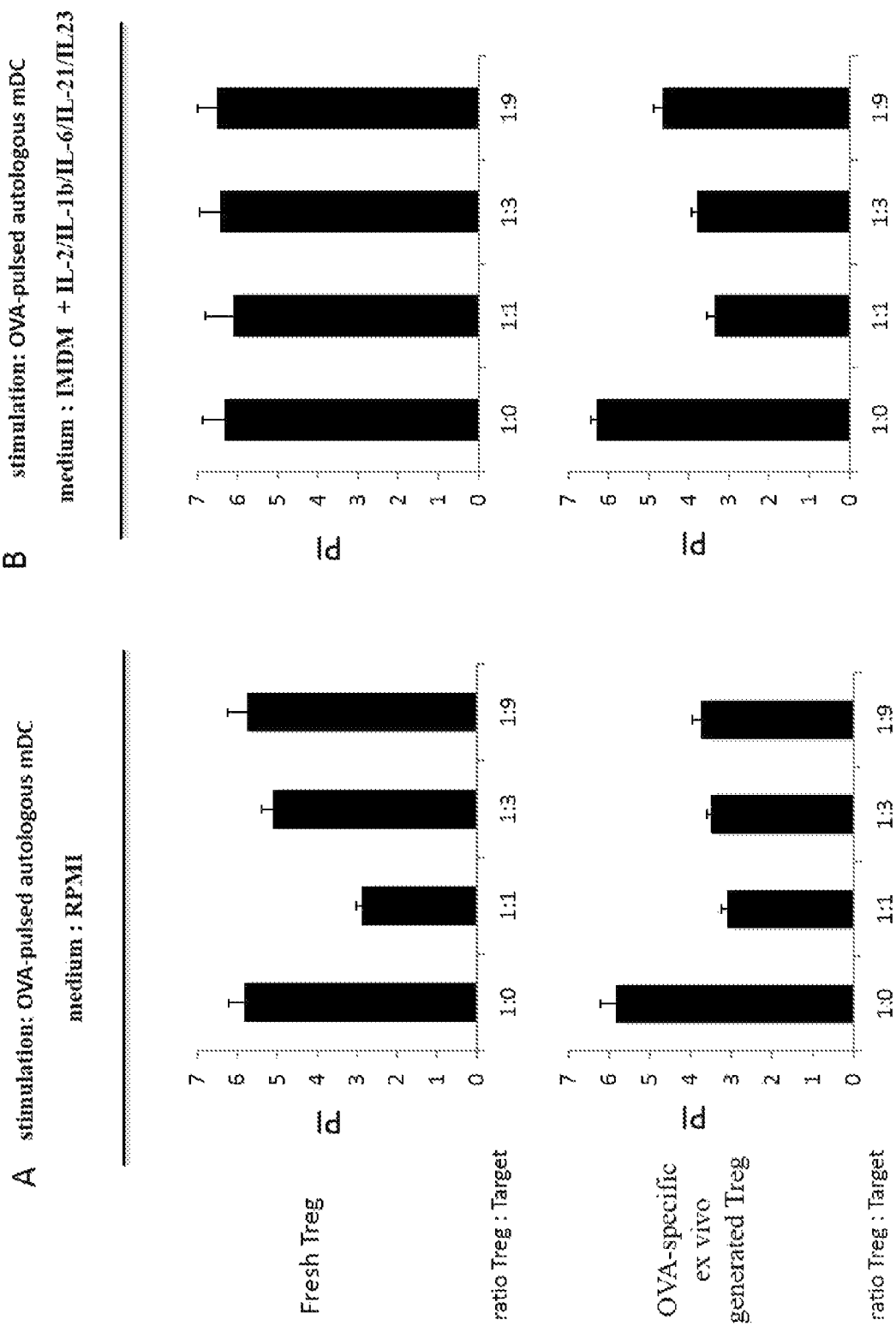
FIG. 8: Suppressive capacity of ex vivo generated OVA-specific Treg after 21 days of culture evaluated with an autologous MLR assay. After magnetic depletion of CD4$^+$ naive T cells, suppressive capacity of ex vivo generated Treg, was evaluated (A) in low and (B) high inflammatory context. CFSE-labeled Tconv (TconvCFSE) were cocultured with ex vivo generated Tregs at different ratios under the indicated stimulations. Proliferation of TconvCFSE was evaluated by the CFSE dilution assay and express as proliferation index (IP). Fresh Treg were used as control.

In addition, these 21-day-expanded-ova-specific CD3+ CD4+ TCRαβ+ MHCII restricted T cells display a similar suppressive activity compared with fresh Foxp3 expressing CD3+ CD4+ TCRαβ+ MHCII restricted T cells, when using both the standard polyclonal cell-cell contact Treg suppression assay (FIG. 7A) and the autologous MLR suppression assay (FIG. 8A).

Furthermore Ova-specific CD3+ TCRαβ+ MHCII restricted T cells maintain their ability to perform suppressive function in pro-inflammatory conditions. When the both functional suppressive assay (FIG. 7B, FIG. 8B) are performed in presence of a highly-inflammatory medium containing IL-2 IL-1 IL-6, IL-21 IL-23 cytokines, while fresh Foxp3 expressing CD3+ CD4+ TCRαβ+ MHCII restricted T cells lose their suppressive capacity under these culture condition of stimulation, the 21-day-expanded-Foxp3 expressing CD3+ CD4+ TCRαβ+ MHCII restricted T cells still maintain their suppressive activity. The maintenance of their suppressive capacity in a high inflammatory context could be ascribed to the fact that they produce low level of IL-17 after 21 days of expansion in the nTreg polarizing medium, when stimulated through CD3 and CD28 in the presence of IMDM medium containing IL-2 IL-1 IL-6, IL-21 IL-23 cytokines (FIG. 10A)

Figure 9:
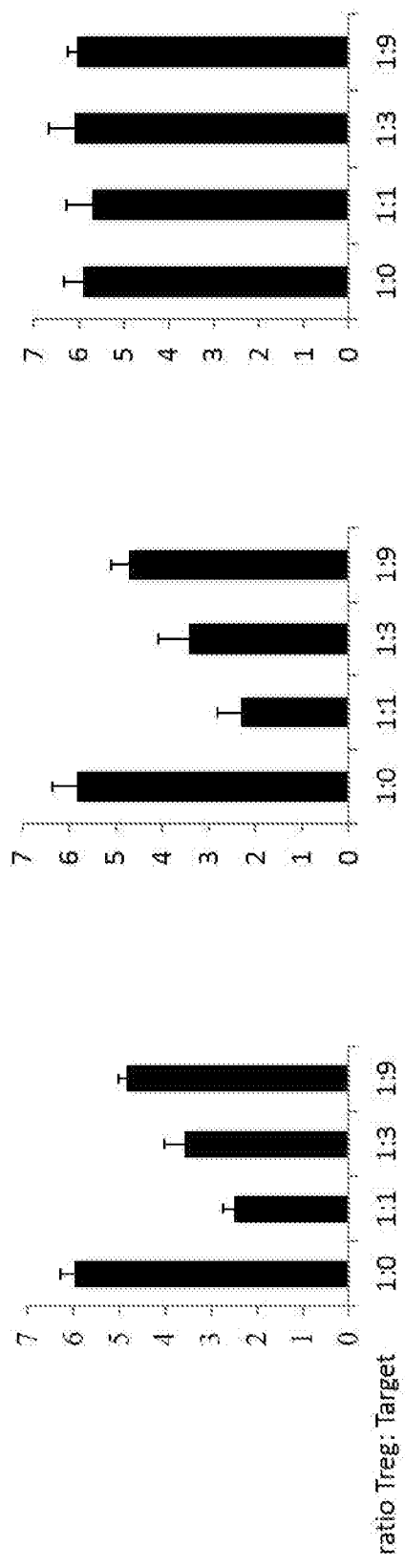
FIG. 9: Combination of TGFβ, RAPA and PGE2 induce the establishment and the expansion of cultured Treg committed to exclusively exert regulatory activity. After 21 days of ex vivo generation in nTreg or TH-17 polarizing medium, suppressive capacity of ex vivo generated OVA-specific Treg was evaluated in the presence of a high inflammatory context inducing medium as described in FIG. 7. Fresh Treg were used as control.
Figure 10:
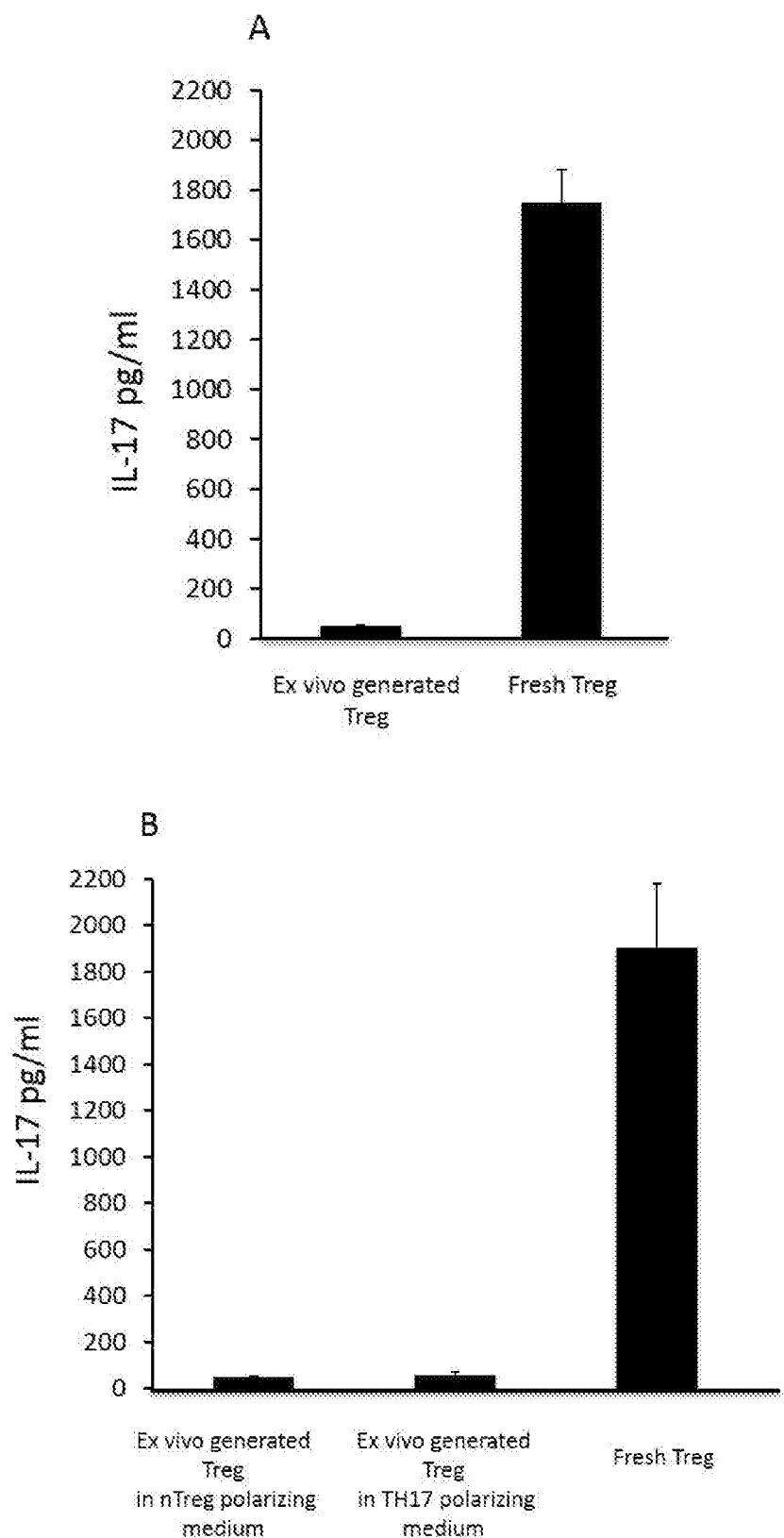
FIG. 10: IL-17 production by stimulated OVA-ex vivo generated Treg. Specific-Treg (A) induced after the first 21 days of culture in nTreg polarizing medium or (B) expanded for 3 weeks in nTreg or TH-17 polarizing medium were tested for their IL-17-producing capacity upon stimulation with aCD3 Ab and aCD28 Ab for 2 days in IMDM medium containing IL-2, IL-1, IL-6, IL-21, and IL-23 cytokines. IL-17 was detected in supernatant culture by ELISA.

To confirm that the Ova-specific CD3+ TCRαβ3+ MHCII restricted T cells are committed to exclusively exert regulatory activity, whatever culture condition of stimulation, after 21 days of expansion in nTreg polarizing medium, the ova-specific-pTreg are further cultured for 3 weeks either in nTreg or TH-17 polarizing medium (IMDM medium containing IL-2 IL-1 IL-6, IL-21 IL-23 cytokines) and were tested for 1) their functional suppressive capacity in the presence of a high inflammatory context (FIG. 9) and 2) for their IL-17-producing capacity when stimulated through CD3 and CD28 as described above (FIG. 10). After a further 21-day-culture either in nTreg or TH-17 polarizing medium, Ova-specific CD3+ TCRαβ+ MHCII restricted T cells not only still retain, in a high inflammatory context, functional suppressive activity (FIG. 9), but also produce low level of IL-17 (FIG. 10B). By contrast fresh Foxp3 expressing CD3+ TCRαβ+ MHCII restricted T cells lose their suppressive function while producing IL-17 in this inflammatory context.

The absence of IL-1R1 expression on the Ova-specific CD3+ TCRαβ+ MHCII restricted T cells could be explained why these specific induced Treg are stable and function effectively in an inflammatory environment. Indeed, as depicted in FIG. 11, when we assessed the expression of IL-1R1 on different population of Treg: a) ex vivo resting Tregs isolated from PBMCs, b) ex vivo expanded Tregs from Treg isolated from PBMCs with polyclonal stimulation, c) polyclonal in vitro induced Treg in the presence of Rapa and TGFβ from conventional T cells isolated from PBMCs and d) in vitro induced Ova-specific CD3+ FOXP3+ T cells in presence of RAPA, TGFβ and PGE2 isolated from naïve CD4+ T cells, We found that IL-1R1 is preferentially expressed on resting, polyclonal expanded/induced Tregs when compared to the induced Ova-specific CD3+ FOXP3+ T cells. We also observe that the stability of the suppressive function is inversely correlated with the IL-1R1 expression.

c—Induction of Autologous CD8-Mediated T-Cell Responses Against Pathogenic CD4+ T Cells Using Apoptotic CD4+ T Cell-Loaded Dendritic Cells.

We have developed an experimental procedure to generate autologous CD8+ T cell lines functionally committed to lyse tumor-antigen specific FOXP3 expressing TCRαβ+ MHCII restricted T cells, pathogenic CD4+ T cells that favour tumor cell immune evasion.

We have first set up optimal conditions for inducing tumor-antigen specific FOXP3+ expressing TCRαβ+ MHCII restricted T cells, as described before. FIG. 12 shows that apoptotic tumor cell lines-pulsed autologous tDCs ("tumor Ag loaded tDC"), in presence of the nTreg polarizing medium comprising the combination of IL-2, TGFβ, PGE2 and rapamycin are able to induce high levels of Foxp3+ expression (in frequency in FIG. 12A and in MFI in FIG. 12B) in antigen specific stimulated naive conventional CD4+ T cells ("Nave Treg") while non-pulsed autologous tDCs ("unloaded tDC"), in presence of the same polarizing medium, were unable to induce Foxp3+ expression in naive conventional CD4+ T cells.

Then, we have established a culture system in which inflammatory DC (inf DC) loaded with apoptotic pathogenic CD4+ T cells cocultured with autologous CD3+ naïve T cells are able to induce the generation of CD8+ T-cell lines against pathogenic CD4+ T cells used to load the dendritic cells. FIG. 13 shows that the two CD8+ clones induced with apoptotic pathogenic CD4+ T cells loaded—inf DC ("mDC") or -TAP-inhibited DC respectively are able to lyse their specific targets, their inducing pathogenic CD4+ T cell clone. However, when both CD8+ clones are tested against an autologous EBV cell line, they are unable to lyse this target.

d) Presence of FOXP3+ Expressing T Cells in Tumor Infiltrating Lymphocytes (TILs) Isolated from Luminal-B Breast Cancer.

Luminal A and B subtypes are both estrogen-receptor-positive (ER+) and low-grade, with luminal A tumors growing very slowly and luminal B tumors growing more quickly. Luminal A tumors have the best prognosis. Luminal B tumors are associated with a poor clinical outcome. We examined by flow cytometry the phenotype of lymphocytes in the TIL isolated from both luminal subtypes breast cancer and found the presence of Foxp3 expression in CD3+ CD4+ TCRαβ+ MHCII restricted T cells. No Foxp3 was detected in TILs extracted from luminal A breast tumor. Moreover, a positive correlation is observed between a high percentage of expression of Foxp3 in CD3+ CD4+ TCRαβ+ MHCII restricted T cells and a poor clinical outcome of breast cancer (FIG. 14).

The invention claimed is:

1. A method for generating ex vivo MHCII restricted CD4$^+$ Foxp3$^+$ regulatory T cells having the following phenotype: CD3$^+$ CD4$^+$ Foxp3$^+$ comprising
culturing in a first culture medium CD3$^+$ CD4$^+$ CD25$^-$ T cells in the presence of a TCRαβ cell activator and adding regulatory T cell differentiation agents to the first culture medium, wherein said regulatory T cell differentiation agents consist of:
i) PGE2,
ii) TGFβ (Transforming growth factor beta),
iii) rapamycin and
iv) IL-2,
for at least 5 days, and
expanding in a second culture medium the MHCII restricted CD4$^+$ Foxp3$^+$ regulatory T cells in the presence of the TCRαβ cell activator and adding regulatory T cell differentiation agents to the second culture medium, wherein said regulatory T cell differentiation agents consist of:
i) PGE2,
ii) TGFβ (Transforming growth factor beta),
iii), rapamycin and
iv) IL-2,
for at least 5 days;
wherein
the TCRαβ cell activator is a polyclonal TCR αβ cell activator or an antigen-specific TCRαβ cell activator, with the caveat that the TCRαβ cell activator is not tolerogenic dendritic cells (DCs) pulsed with at least one self-peptide antigen;
and wherein said expanding step produces MHCII restricted CD4$^+$ Foxp3$^+$ regulatory T cells that remain stable when placed in inflammatory conditions.

2. The method according to claim 1, wherein the polyclonal TCRαβ cell activator is an anti-CD3 antibody or an anti-TCRαβ antibody.

3. The method of claim 1, wherein the MHCII restricted CD4$^+$ Foxp3$^+$ regulatory T cells produced in said expanding step lack IL-1R1 expression.

* * * * *

SEQUENCE LISTING

<160> NUMBER OF SEQ ID NOS: 14

<210> SEQ ID NO 1

```
<211> LENGTH: 37
<212> TYPE: DNA
<213> ORGANISM: Artificial Sequence
<220> FEATURE:
<223> OTHER INFORMATION: Synthetic primers FOXP3_TSDR fwd

<400> SEQUENCE: 1
atatttttag atagggatat ggagatgatt tgtttgg                              37

<210> SEQ ID NO 2
<211> LENGTH: 31
<212> TYPE: DNA
<213> ORGANISM: Artificial Sequence
<220> FEATURE:
<223> OTHER INFORMATION: Synthetic FOXP3_TSDR rev

<400> SEQUENCE: 2
aataaacatc acctaccaca tccaccaaca c                                   31

<210> SEQ ID NO 3
<211> LENGTH: 29
<212> TYPE: DNA
<213> ORGANISM: Artificial Sequence
<220> FEATURE:
<223> OTHER INFORMATION: Synthetic TSDR-Forward

<400> SEQUENCE: 3
ggtttgtatt tgggttttgt tgttatagt                                      29

<210> SEQ ID NO 4
<211> LENGTH: 34
<212> TYPE: DNA
<213> ORGANISM: Artificial Sequence
<220> FEATURE:
<223> OTHER INFORMATION: Synthetic TSDR-Reverse

<400> SEQUENCE: 4
ctataaaata aaatatctac cctcttctct tcct                                34

<210> SEQ ID NO 5
<211> LENGTH: 14
<212> TYPE: DNA
<213> ORGANISM: Artificial Sequence
<220> FEATURE:
<223> OTHER INFORMATION: Synthetic FAM-labeled methylated probe

<400> SEQUENCE: 5
cggtcggatg cgtc                                                      14

<210> SEQ ID NO 6
<211> LENGTH: 18
<212> TYPE: DNA
<213> ORGANISM: Artificial Sequence
<220> FEATURE:
<223> OTHER INFORMATION: Synthetic VIC-labeled unmethylated probe

<400> SEQUENCE: 6
tggtggttgg atgtgttg                                                  18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer promoter

<400> SEQUENCE: 7
```

```
accgtacagc gtggttttc                                         20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer promoter

<400> SEQUENCE: 8
ctacctccct gccatctcct                                        20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer CNS1

<400> SEQUENCE: 9
cccaagccct atgtgtgatt                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer CNS1

<400> SEQUENCE: 10
gtgtgtcagg ccttgtgcta                                        20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer CNS2

<400> SEQUENCE: 11
gtcctctcca caacccaaga                                        20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer CNS2

<400> SEQUENCE: 12
gacaccacgg aggaagagaa                                        20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer CNS3

<400> SEQUENCE: 13
aggtgccgac ctttactgtg                                        20

<210> SEQ ID NO 14
<211> LENGTH: 20
<212> TYPE: DNA
```

```
<213> ORGANISM: Artificial Sequence
<220> FEATURE:
<223> OTHER INFORMATION: Synthetic primer CNS3

<400> SEQUENCE: 14
acaatacggc ctcctcctct                                              20
```